(12) United States Patent
Ralph et al.

(10) Patent No.: US 7,695,473 B2
(45) Date of Patent: Apr. 13, 2010

(54) ADJUSTABLE BONE PLATE

(75) Inventors: James D. Ralph, Bethlehem, PA (US); Stephen L. Tatar, Montville, NJ (US); Thomas N. Troxell, Pottstown, PA (US)

(73) Assignee: BioDynamics LLC, Englewood, NJ (US)

( * ) Notice: Subject to any disclaimer, the term of this patent is extended or adjusted under 35 U.S.C. 154(b) by 240 days.

(21) Appl. No.: 11/334,696

(22) Filed: Jan. 18, 2006

(65) Prior Publication Data

US 2007/0173841 A1    Jul. 26, 2007

(51) Int. Cl.
*A61B 17/80* (2006.01)
(52) U.S. Cl. ..................................................... 606/71
(58) Field of Classification Search .................. 606/60, 606/69, 280, 70, 71, 286, 291, 297, 298
See application file for complete search history.

(56) References Cited

U.S. PATENT DOCUMENTS

| | | | |
|---|---|---|---|
| 6,238,396 B1 * | 5/2001 | Lombardo | 606/86 A |
| 6,306,136 B1 * | 10/2001 | Baccelli | 606/279 |
| 6,666,867 B2 | 12/2003 | Ralph et al. | |
| 7,044,952 B2 * | 5/2006 | Michelson | 606/71 |
| 7,090,676 B2 * | 8/2006 | Huebner et al. | 606/71 |
| 7,318,825 B2 * | 1/2008 | Butler et al. | 606/71 |
| 7,331,961 B2 * | 2/2008 | Abdou | 606/71 |
| 2004/0092939 A1 | 5/2004 | Freid et al. | |
| 2004/0102778 A1 | 5/2004 | Huebner et al. | |
| 2005/0260247 A1 | 11/2005 | Ralph et al. | |
| 2006/0235398 A1 * | 10/2006 | Farris et al. | 606/69 |

FOREIGN PATENT DOCUMENTS

WO    WO 03071966 A1 *    9/2003
WO    WO 2005060846 A1 *    7/2005

* cited by examiner

*Primary Examiner*—Eduardo C Robert
*Assistant Examiner*—Ellen C Hammond
(74) *Attorney, Agent, or Firm*—Norris McLaughlin & Marcus, P.A.

(57) ABSTRACT

The invention pertains to adjustable bone plates which comprise one or more sets of first members and second members. The first members and second members are releaseably secured to each other by attachment means and locking means, and two or more set of first members and second members are connected by bridging means. The longitudinal and lateral dimensions of the bone plates may be adjustable.

1 Claim, 15 Drawing Sheets

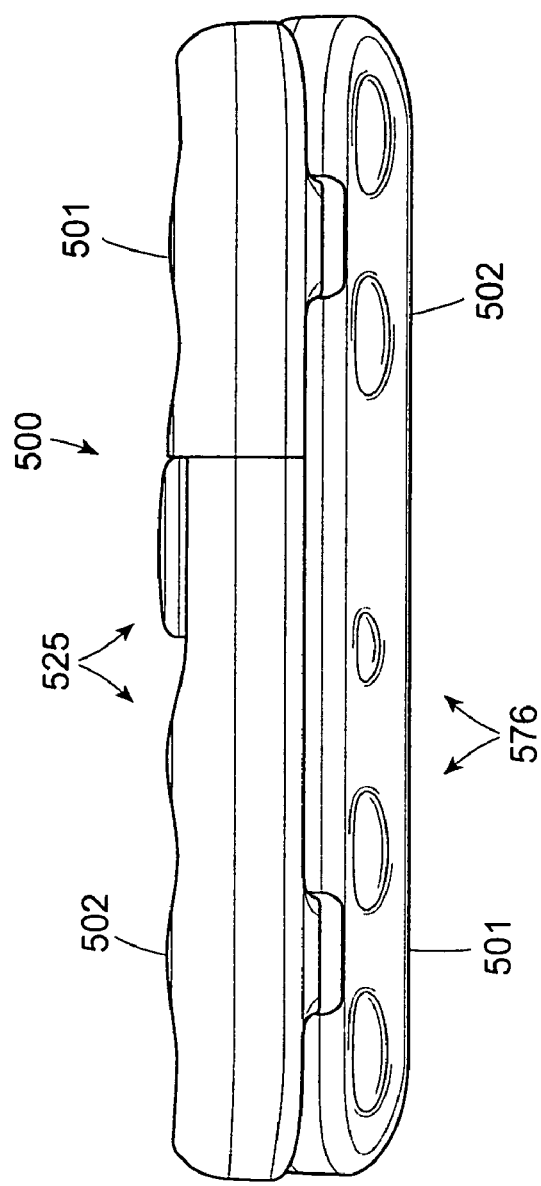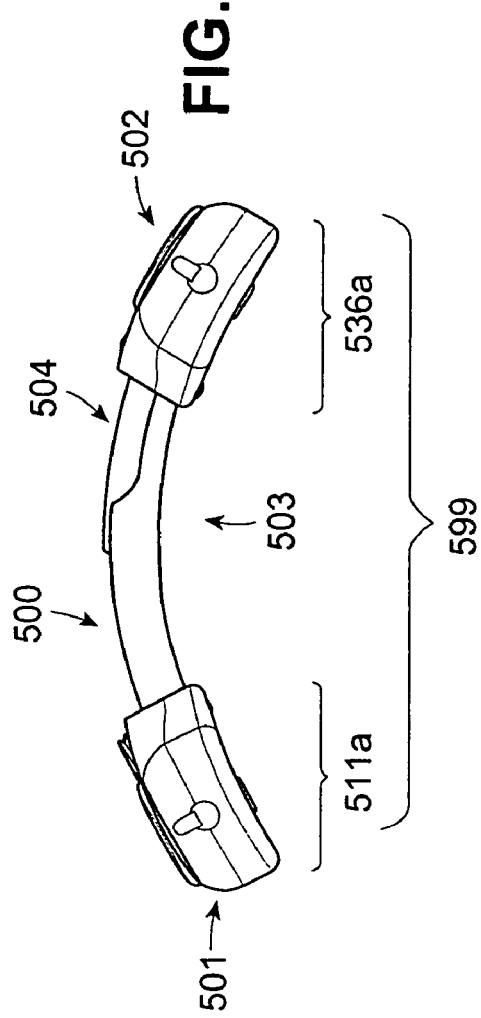

ADJUSTABLE BONE PLATE

BACKGROUND OF THE INVENTION

1. Field of the Invention

The invention pertains to adjustable bone plates which comprise one or more sets of first and second members releaseably secured to each other. The members are capable of sliding thereby allowing the surgeon to adjust the longitudinal length of the bone plate and also to move pieces of broken bone closer to each other prior to setting the longitudinal length of the bone plate. The invention also pertains to bone plates that may be adjusted in both a longitudinal and lateral dimension.

2. The Relevant Art

Conventional bone plates have fixed dimensions and multiple holes for accommodating bone screws. Surgeons generally use bone plates to join sections of fractured bone by placing the bone plate atop the fracture, inserting bone screws through the holes in the plate which overlie the healthy part of the bone and securing the bone about the fracture. Bone plates of many sizes are provided for the surgeon, each having a number of holes so that the surgeon can arrange the plate over the fracture and have bone screw holes available above the healthy bone.

Direct Compression Plates ("DCP") are also available to stabilize fractured bone. DCP generally have angulated openings, through which screws are "toed" into the bone with the tightening of the toed screws operating to move the bone, slightly, under the DCP. DCP have been used to move bone pieces on either side of the fracture closer together. However, with a DCP, only slight and not easily controllable movements occur. Generally, the underlying bone is pulled into place by the threads of a screw, providing no control over the twisting or turning of the bone, and the bending of the plate. In addition, the bone is pulled at an angle to the attached plates, which can result in a cocked bone or at an angle to the longitudinal direction of the bone. This angulation, together with the micromotion in the bone, has led to backing out of the screws after the bone plate is secured to the bone.

Thus, there is a need for bone plates which are adjustable that allow the surgeon to move the broken pieces of bone while inhibiting or preventing the bone from twisting or cocking either during the process of applying the bone plate to the fractured bone or afterwards.

SUMMARY OF THE INVENTION

The bone plate, or bone plate assembly, of the invention comprises one or more sets of first member and second member. In each set, a first member and a second member are releaseably secured to each other through attachment means. The attachment means provides each first member and second member with the capability of being releaseably secured in a manner which allows longitudinal adjustment of the location of the first member and second member with relation to each other thereby allowing the bone plate assembly to have an adjustable longitudinal length or dimension. The attachment means generally functions with a locking means which restricts or inhibits the longitudinal movement of the members thereby setting the longitudinal length of the bone plate assembly. For example, in use, the surgeon may secure a first member to one side of a break in a broken bone and secure the second member to another side of the break of the broken bone and then can move one or both members to bring the pieces of broken bone together. Once the surgeon has moved the pieces of bone as desired for healing, the surgeon may then apply the locking means to set the longitudinal length of the bone plate assembly. In embodiments of the invention, more than one set of first member and second member can be applied to broken bones with the set of first member or second member connected to each other, such as through bridging means, to provide adjustment to the lateral dimension of the bone plate assembly.

The attachment means for example may comprise a flange in one member and corresponding recess in another member. The flange is capable of sliding within the recess thus providing the bone plate with adjustability. Another example of an attachment means is a one or more connecting rods which are capable of translating within rod bores in the first member and/or second member.

The locking means may be any mechanical device that can prevent the first member and second member from physically moving in relation to each other. In general, the locking means may be one or more of the following: heat shrinking, glue, molding of the first member and second member together, screws, pins or anchors, and combinations of these.

For example, the locking means may be a large head screw which engages a slot in the flange of one member and a screw bore at the recess of a second member which, upon tightening, locks the flange within the recess thereby preventing the first member and second member from moving in relation to each other. Another example of a locking means is a set screw which engages a locking means bore on the first member and/or second member effectively crushing elements of the first member and second member over the attachment means creating frictional forces that preclude movement of the first member and second member with respect to each other. In an embodiment of the invention, the attachment means is one or more connecting rods which translate within rod bores on the first member and/or second member and a set screw applied within the locking means bore of the first member and/or second member forces the walls of the rod bores against the connecting rods creating frictional forces between the outer surfaces of the connecting rods and the rod bore walls which preclude movement. Other locking means include physical bonding such as a biocompatible adhesive or heat which forms a physical bond between the first member and second member, such as between surfaces of the flange and recess. For example, once the first member and second member are set in place the surgeon can apply an adhesive or other bonding agent which secures the first member and second member in a fixed relationship to each other or can apply heat which effectively melts the surfaces of the first member or second member that are aligned and in contact with each other causing the melted material of each plate to mix together thereby physically connecting the two members when the heat source is removed and the first member and second member cool.

The adjustable bone plate may further comprise bridging means which allows two or more sets of adjustable first member and second member to be connected to each other to form a bone plate assembly that has adjustability with respect to both the longitudinal and lateral dimensions. In this embodiment of the invention, the adjustable bone plate comprises one or more windows to allow the surgeon to observe broken pieces of bone coming together while the longitudinal and/or lateral dimensions of the bone plate are being adjusted. For example, each the adjustable bone plate assembly may comprise one or more bridging rods which are capable of translating within one or more bridging rod bores in the first member and/or second member. The bridging means may also have the same or similar structure as the attachment means discussed above.

The adjustable bone plate assemblies may further comprise a bridge locking means for use in conjunction with the bridging means to inhibit or restrict movement of one set of first member and second member in relation to an adjoined set of first member and second member thereby setting the lateral dimension of the adjustable bone plate assembly. For example, the bridge locking means may be screw member, such as a set screw, which is screwed into a bore on a first member and/or second member and directly interfaces a surface of the bridging means thereby inhibiting or preventing the movement of one set of first and second member in relation to an adjoined set of first and second members by preventing or inhibiting the translation of the bridging means within the bridging means bores. In addition to a set screw or other screw member, the bridge locking means also be any of the locking means discussed above.

The bone plates may be made by a biologically acceptable material. Combinations of materials can be used.

The invention further pertains to the methods for applying the bone plate assembly for healing broken bones of a patient. For example, in one method only one set of first member and second member is used. In this method, the first member or second member is placed over a bone on one side of the break and the first member or second member is placed over the bone on the other side of the break and the first member and second member are then releasably secured to each other with the attachment means and/or locking means. The bone screws or other bone attachment means may be applied to secure the first member and second member to the bone of a patient by translating bone screws or other bone attachment means through bone screw holes in the first member and second member and into the bone after the attachment means is engaged, such as being partially or loosely engaged to allow for movement. In an embodiment of the invention, the bone attachment means may be applied prior to engagement of the attachment means. As such, the first member and second member may be releaseably secured to each other either prior to the bone plate being secured to the bone of a patient or after the bone plate is secured to the bone of a patient. Bone attachment means are bone screws, surgical fasteners or any other device capable of securing the bone plates, or any component of the bone plate, to the bone of a patient. Also, the first member and second member may first be releasably secured and then placed over the broken bone with one member on one side and another member on another side and then the bone screws are applied to secure the bone plate assembly to the broken bone. In any event, once the first member and second member are secured to the bone, the surgeon may then move the first member or second member to bring the pieces of the broken bone together and then further apply or tighten the attachment means and/or locking means to prevent further movement of the first member and second member to fix the longitudinal dimension of bone plate assembly and set the bone in a place for healing.

In a further embodiment, the method comprises applying one or more additional sets of first member and second member. In this embodiment a first member and second member set are applied to the broken bone of a patient, generally as discussed above, and then the bridging means is applied and next a second first member and second member set is applied. Further, first member and second member sets may be applied with the bridging means between each additional set and the prior set of first member and second member. Each set of first member and second member may be adjusted with respect to the longitudinal dimension of each, as discussed above, and the lateral dimension may be adjusted by moving sets of the first member and second member in conjunction with the bridging means. Once the pieces of broken bone have been moved to the desired location, the longitudinal and lateral dimension of the bone plate assembly can be fixed by applying and/or tightening the attachment means and/or locking means (for the longitudinal direction) and the bridge locking means (for the lateral direction). Also, in an embodiment of the invention, the method comprises having the longitudinal and/or lateral dimensions of the bone plate fixed prior to applying the bone plate to the bone of a patient by securing the bone plate to the bone of a patient. The location of each first member and second member with respect to various sides of the break will depend on the nature of the broken bone. For example, a bone may have bisecting breaks in which case each separate first member and second member in the bone plate assembly, such as one having two sets of first member and second member connected by bridging means, may be secured in different sections of the broken bone.

BRIEF DESCRIPTION OF THE DRAWINGS

FIG. 13 is a side view of an adjustable bone plate in accordance with an embodiment of the invention.

FIG. 14 is an end view of an adjustable bone plate in accordance with an embodiment of the invention.

DETAILED DESCRIPTION OF THE INVENTION

Figure 1:
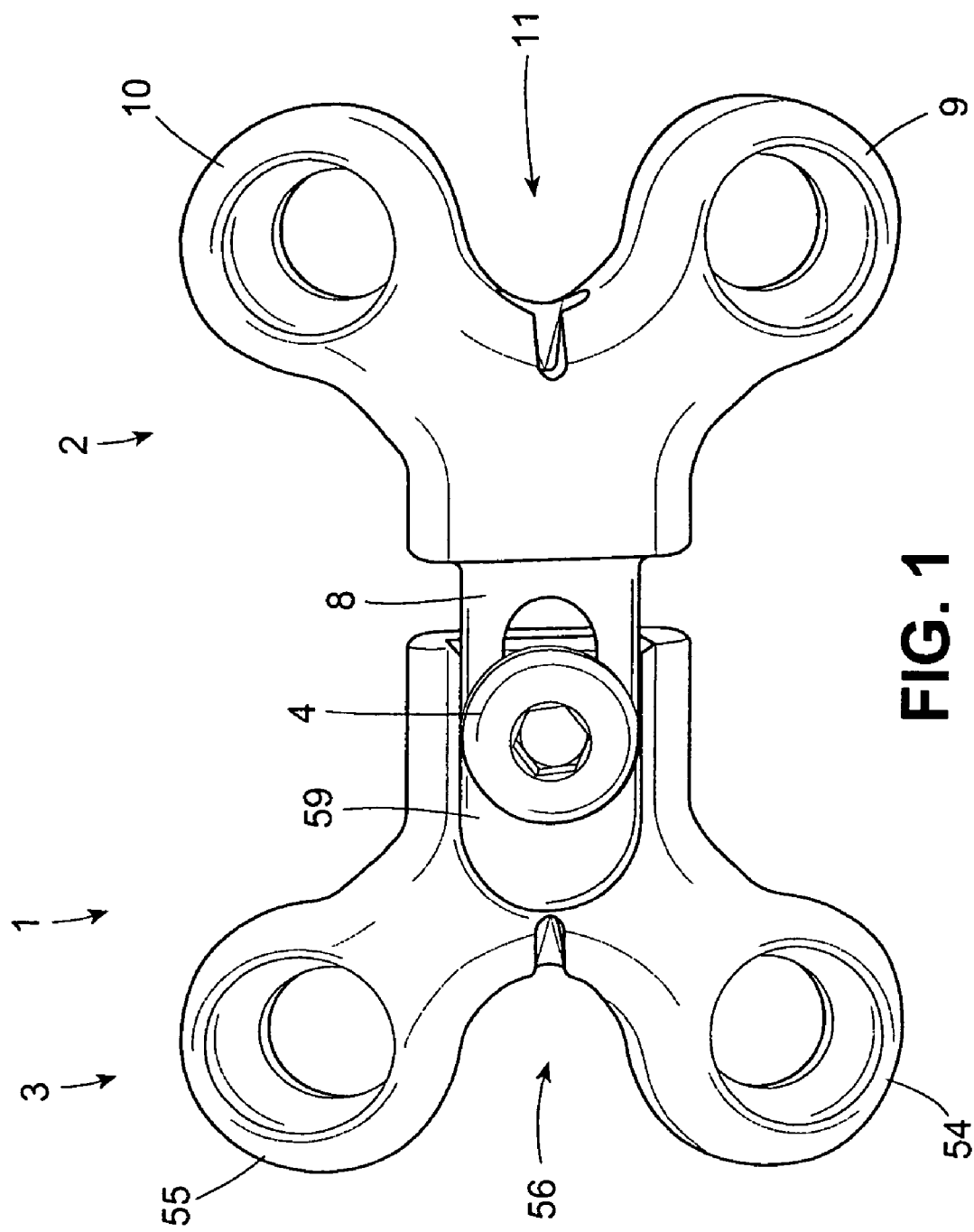
FIG. 1 is a perspective view of an adjustable bone plate in accordance with an embodiment of the invention.

FIGS. 1-7 show a bone plate assembly 1, in an embodiment of the invention, wherein the bone plate assembly comprises a first member 2, a second member 3 and a locking means 4. In this embodiment of the invention each of the first member and second member comprises two ends and at least one end of each has one or more, preferably, two circular elements. Each circular element has at least one bone screw bore therein. In this embodiment of the invention, one of the ends of each of the first member and second member comprise or may accommodate the attachment means such that the first member and second member may be integrated into an adjustable bone plate assembly. In the embodiment of the invention shown in FIGS. 1-7, the attachment means comprises a flange 8 at the second end of the first member and a corresponding recess 59 proximate to the second end of the second member and extending from the second end to a point between the first end and second end of the second member.

Figure 2:
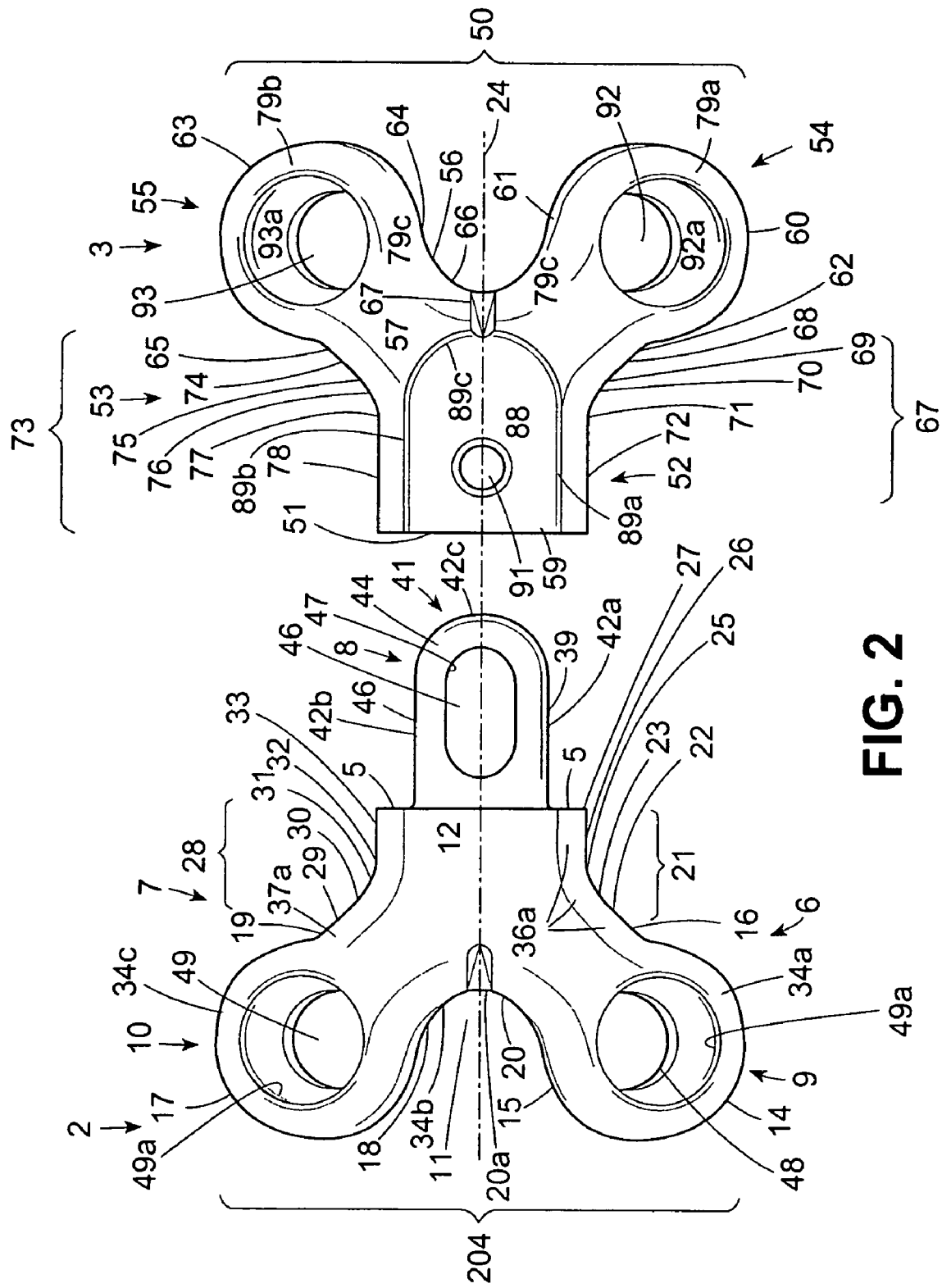
FIG. 2 is a top view of the first member and second member of an adjustable bone plate in accordance with an embodiment of the invention.
Figure 3:
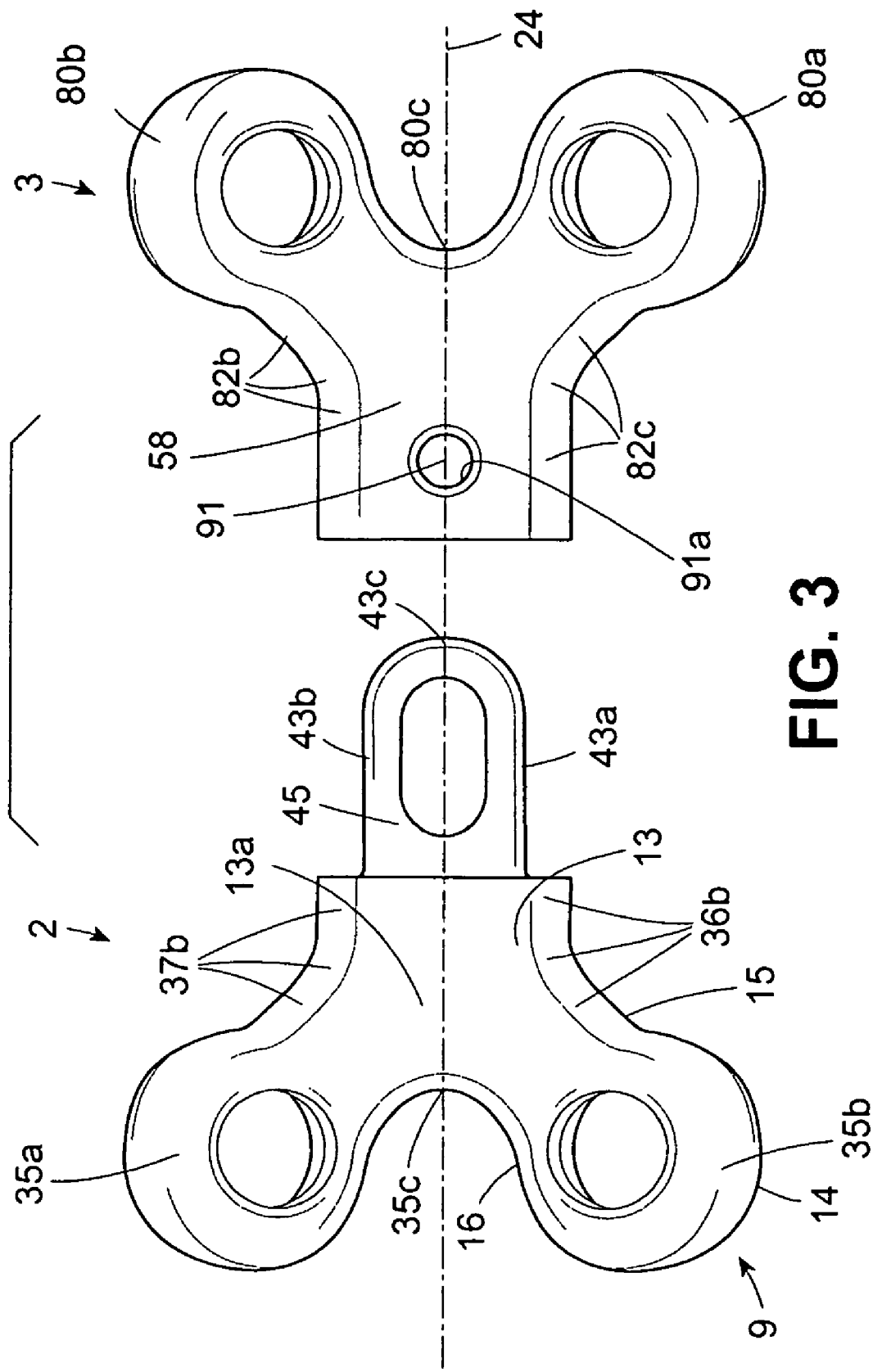
FIG. 3 is a bottom view of the first member and second member of an adjustable bone plate in accordance with an embodiment of the invention.

As shown in FIGS. 2 and 3, the first member comprises a first member first end 204, a first member second end 5, a first member forward side 6 and a first member distal side 7. The flange 8 protrudes from the first member second end 5. The first member first end 204, in the embodiment of the invention shown in FIGS. 1-7, comprises a first member forward circular element 9 and a first member distal circular element 10 joined by a first member center section 11 having curvature. The first member 2 further comprises a first member upper surface 12 and a first member lower surface 13 which comprises a first member lower surface curved section 13a which is generally a concave arcuate section which further facilitates the snug fit of the first member and adjustable bone plate against the curvature of the bone structure.

The first member forward circular element 9 has a continuous side 14 which extends from a first member first forward termination point 15 to a first member second forward termination point 16 such that the side is circular or semi-circular in orientation. Likewise, the first member distal circular element 10 has a continuous side 17 which extends from a first member first distal termination point 18 to a first member second distal termination point 19. The first member center section 11 is adjacent to the first member first forward termination point 15 and the first member first distal termination point 18, and extends from the first member first forward termination point 15 to the first member first distal termination point 18. In a preferred embodiment, the first member first forward termination point 15 and the first member first distal termination point 18 oppose each other and the first member center section side 20 of the first member center section 11 has curvature creating a void between the first member forward circular element 9 and first member distal circular element 10 having semicircular surface which is such that the sides of the first member forward circular element 9, first member center section 11 and first member distal circular element 10 represent a continuous curved surface. The first member center section may also comprise one or more locking slots that may be engaged by closure means which may be provided with the bone plate assembly, to assist in moving of the first member when engaged with the second member forming the adjustable bone plate. The first member center section 11, in this embodiment of the invention, comprises a first member locking slot 20a at about the centerline of the first member (which is shown for example as centerline 24 on FIGS. 2 and 3 along both the first member 2 and second member 3).

The first member 2, in the embodiment of the invention shown in FIGS. 1-7, and particularly in FIG. 2, further comprises a first member forward side edge 21 extending from the first member second forward termination point 16 to the first member second end 5. Preferably, the first member forward side edge comprises a first member first forward edge section 22 adjacent to the first member second forward termination point 16 and extending to a point more proximate to the first member second end 5 and may be slanted from a forward position at the first member second forward termination point 16 to a more distal position at a first member third forward termination point 23, i.e., slanted towards the centerline 24 of the first member. Adjacent to the first member first forward edge section 22 is a first member second forward edge section 25, which extends to a first member fourth forward termination point 26. Adjacent to the first member second forward edge section 22 is a first member third forward edge section 27 which extends to the first member second end 5 and is generally parallel to the centerline 24. In a preferred embodiment, because the first member first forward edge section 22 is slanted with respect to the centerline of the first member and the first member third forward edge section 27 is generally parallel to the centerline 24, the first member second forward edge section 25 may have curvature to provide a curved surface to join the first member first forward edge section 22 and a first member third forward edge section 27 such that the first member forward side edge 21 has a continuous curved surface without any sharp edges joining the sides.

As shown in FIGS. 1-7, and particularly in FIG. 2, the first member 2 further comprises a first member distal side edge 28 extending from the first member second distal termination point 19 to the first member second end 5. Preferably, the first member distal side edge 28 comprises first member first distal edge section 29 adjacent to the first member second distal termination point 19 and extending to a point more proximate to the first member second end 5 and may be slanted from a distal position at the first member second distal termination point 19 to a more forward position at a first member third distal termination point 30, i.e. slanted towards the centerline 24 of the first member. Adjacent to the first member first distal edge section 29 is a first member second distal edge section 31, which extends to a first member fourth distal termination point 32. Adjacent to the first member second distal edge section 29 is a first member third distal edge section 33 which extends to the first member second end 5 and is generally parallel to a centerline 24. In a preferred embodiment, because the first member first distal edge section 29 is slanted with respect to the centerline 24 of the second member and the first member third distal edge section 33 is generally parallel to the centerline, the first member second distal edge section 31 may have curvature to provide a curved surface to join the first member first distal edge section 29 and a first member third distal edge section 33 such that the first member distal side has a continuous curved surface without any sharp edges joining the sides.

Referring for example to FIGS. 2 and 3, each of the continuous sides of the first member forward circular element and first member distal circular element, as well as the first member center section side have upper longitudinally curved sections (34a, 34b and 34c) and lower longitudinally curved sections (35a, 35b, and 35c) which provide the sides with concave curvature. Also the edges of the first member forward side and first member distal side have upper longitudinally curved sections (36a and 36b) and lower longitudinally curved sections (37a and 37b). These longitudinally curved sections provide the sides and edges of the first member with concave curvature and an uninterrupted longitudinal curve which allow the bone plates to fit snugly against the curvature of the bone structure. The second end, however, may not have longitudinally curved sections.

Figure 4:
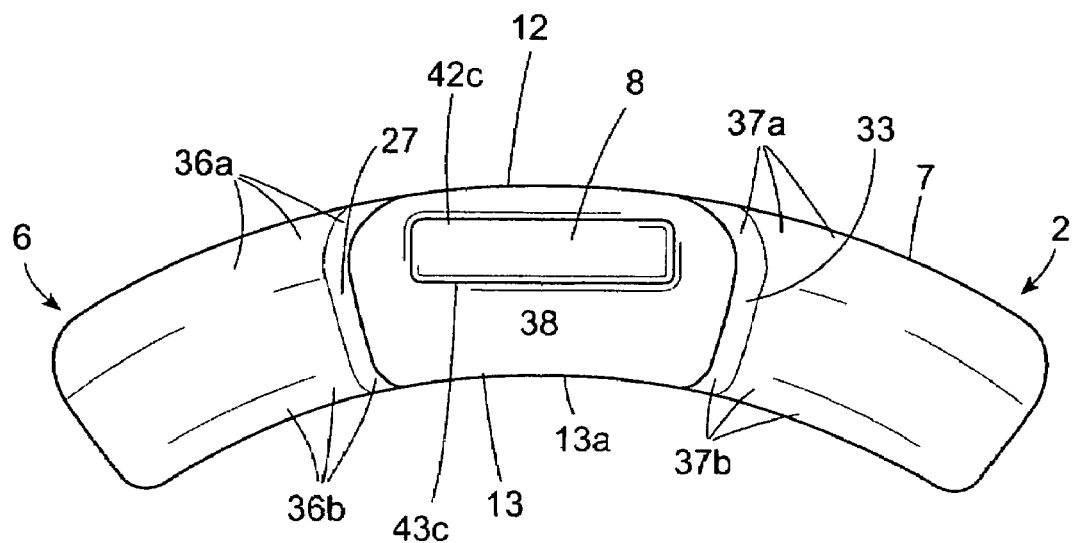
FIG. 4 is an end view of a first member of an adjustable bone plate in accordance with an embodiment of the invention.
Figure 16:
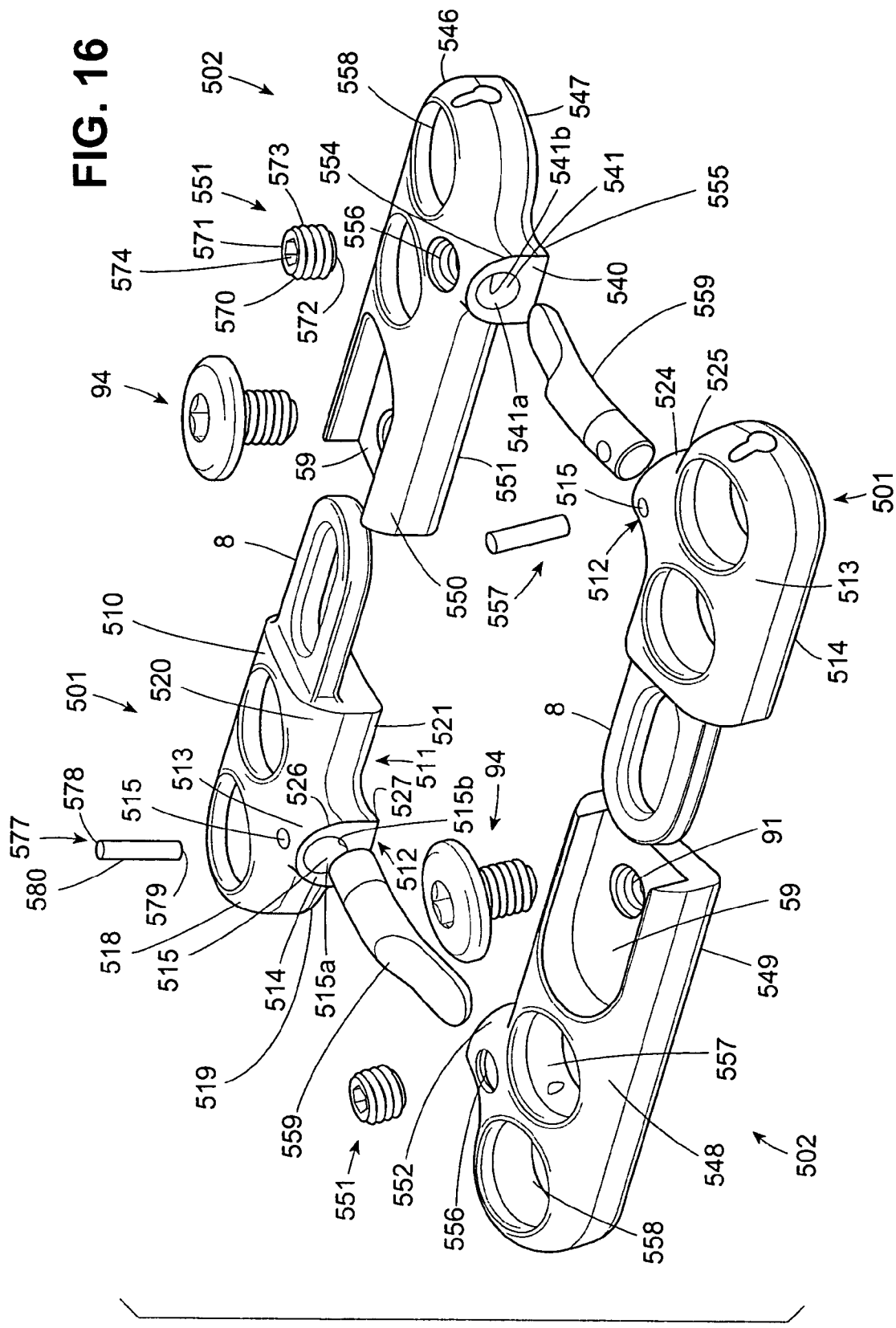
FIG. 16 is an exploded perspective view of an adjustable bone plate in accordance with an embodiment of the invention.
Figure 19:
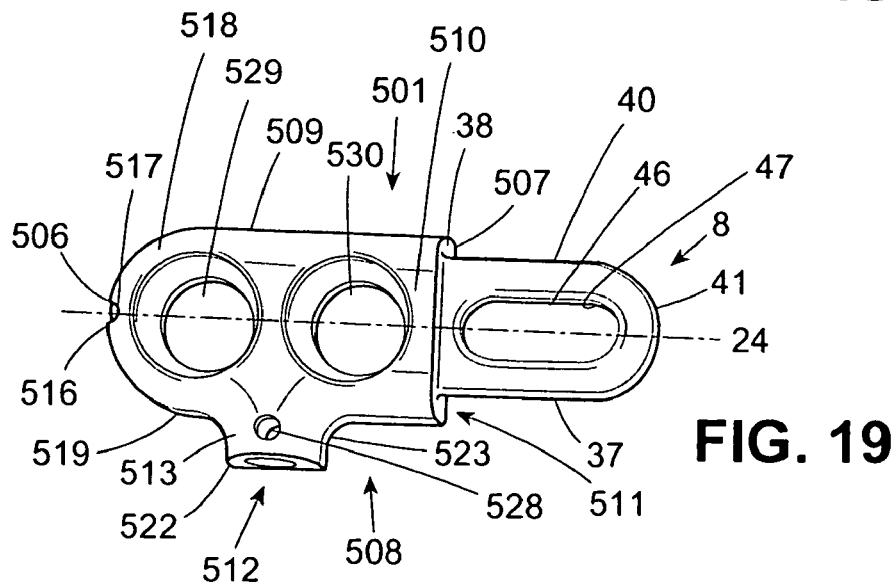
FIG. 19 is a top view of second member of an adjustable bone plate in accordance with an embodiment of the invention.

The second end 5 of the first member (2 and 501) has, as shown in FIG. 4, and also in FIGS. 16 and 19 with respect to other embodiments of the invention, a second end surface 38 which is generally flush and extends from the forward side to the distal side of the first member, such as from the third forward edge section 27 to the third distal edge section 33. The flange 8 protrudes from the second end surface 38 of the first member, preferably, as shown in the drawings more proximate to the first member upper surface (12 and 510) than the first member lower surface (13 and 511). As shown in the drawings, the flange has a flange forward side 39, flange distal side 40 and a flange end 41. The flange forward side 39 generally extends from the second end surface 38 proximate to the forward side of the first member to the flange end 41, and the flange distal side generally extends from the second end surface 38 proximate to the distal side of the first member to the flange end 41. The flange forward side 39 and flange distal side 40 may protrude at defined angles to each other or may, as shown in the drawings, be parallel to each other. The flange end extends between the ends of the flange forward side 39 and flange distal side 40 and may extend perpendicular to the flange forward side 39 and flange distal side 40, or at any angle or orientation. In the embodiment of the invention shown in the drawings, the flange end is a convex curved piece which provides the flange with a continuous curved profile at the end. The flange further comprises, particularly as shown in FIGS. 2-4, upper longitudinally curved sections (42a, 42b and 42c) and lower longitudinally curved sections (43a, 43b, and 43c) which facilitate sliding of the flange into the recess, as described below.

The flange comprises a flange upper surface 44 and a flange lower surface 45. The flange also comprises an opening 46 which extends from the flange upper surface 44 to the flange lower surface 45. The opening 46 is defined by a flange opening inner wall 47. The opening may be any geometric shape such as, as shown in the drawings, an oval. The opening 46 of the flange is generally centered on the center line 24 of the first member. As shall be discussed below, the flange operates in conjunction with the recess of the second member and locking means and has a shape consistent with the shape of the recess and a size which enables the flange and the first member to move or slide in a longitudinal direction to vary the longitudinal length of a bone plate when the first member is conjoined with a second member to form the bone plate.

The first member comprises one or more bone screw bores. In the embodiment of the invention shown in FIGS. 1-7, the first member comprises a first member forward bone screw bore 48 proximate to the forward circular element 9, and a first member distal bone screw bore 49, proximate to the distal circular element 10. The first member forward bone screw bore 48 extends from the upper surface to the lower surface of the first member and is defined by first member forward bone screw bore inner wall 48a there between. The first member distal bone screw bore 49 extends from the upper surface to the lower surface of the first member and is defined by first member distal bone screw bore inner wall 49a there between. The bone screw bores are generally cylindrical and when a bone screw or other bone attachment means is inserted into the bone screw bore, the top surface of the bone screw or other bone attachment means is flush, or about flush, with the upper surface of the longitudinal plate such that they are recessed into the first member longitudinal plate. Also, the bone screws will lock with the bone screw bores and also the bone of the patient.

As discussed above, the first member may optionally have curvature, for example, the first member bottom surface comprises the first member bottom surface curved section 13a which is generally a concave arcuate section. This means that the upper surface has a convex appearance and the first member when observed from the end, as shown particularly in FIG. 4, has a curved appearance. Because the first member has curvature, when bone screws or other bone attachment means are inserted into the first member forward bone screw bore 48 and the first member distal bone screw bore 49, the ends of the bone screws or other bone attachment means within the bone point towards each other, e.g., toe, which provides greater assurance that the bone screws or other bone attachment means will not pull out of the bone. This arrangement may also inhibit twisting of the bone plate.

In the embodiment of the invention shown in FIGS. 1-7, particularly referring to FIGS. 2 and 3, the second member comprises a second member first end 50, a second member second end 51, a second member forward side 52 and a second member distal side 53. The second member first end 50 comprises a second member forward circular element 54 and a second member distal circular element 55 joined by a second member center section 56 having curvature. The second member further comprises a second member upper surface 57 and a second member lower surface 58 which comprises a curved section 58a which is generally a concave arcuate section that facilitates the snug fit of the bone plate against the curvature of the bone structure. The second member further comprises a recess 59 on the second member upper surface 57 which extends from the second member second end 51 to a point proximate to the second member first end 50, such as, as shown in FIGS. 2-4, proximate to the second member center section 56.

The second member forward circular element 54 has a second member forward continuous side 60 which extends from a second member first forward termination point 61 to a second member second forward termination point 62 such that the second member forward continuous side is circular or semi-circular in orientation. Likewise, the second member distal circular element 55 has a second member distal continuous side 63 which extends from a second member first distal termination point 64 to a second member second distal termination point 65. The second member center section is adjacent to the second member first forward termination point 61 and the second member first distal termination point 64, and extends from the second member first forward termination point 61 to the second member first distal termination point 64. In a preferred embodiment, the first forward termination point 61 and the first distal termination point 64 oppose each other and the second member center section side 66 of the second member center section 56 has curvature creating a void between the second member forward circular element 60 and second member distal circular element 63 having semi-circular surface which is such that the sides of the forward circular element, center section and distal circular element of the second member represent a continuous curved surface. The second member center section may also comprise one or more locking slots which may be engaged by closure means provided with the bone plate assembly, to assist in moving of the first member when engaged with the second member forming the bone plate. In the embodiment of the invention shown in the drawings, the center section comprises a locking slot 67 at about the centerline 24 of the second member.

The second member 3, in this embodiment of the invention, further comprises a second member forward side edge 67 extending from the second member second forward termination point 62 to the second member second end 51. Preferably, the forward side edge comprises a second member first forward edge section 68 adjacent to the second member second forward termination point 62 and extending to a point more proximate to the second member second end 51 and may be slanted from a forward position at the second member second forward termination point 62 to a more distal position at a second member third forward termination point 69, i.e., slanted towards the centerline 24 of the second member. Adjacent to the second member first forward edge section 68 is a second member second forward edge section 70, which extends to a second member fourth forward termination point 71. Adjacent to the second member second forward edge section 71 is a second member third forward edge section 72 which extends to the second member second end 51 and is generally parallel to the centerline 24. In a preferred embodiment, because the second member first forward edge section 69 is slanted with respect to the centerline 24 of the second member and the second member third forward edge section 72 is generally parallel to the centerline 24, the second member second forward edge section 70 may have curvature to provide a curved surface to join the second member first forward edge section 69 and second member third forward edge section 72 such that the second member forward side edge has a continuous curved surface without any sharp edges joining the sides.

The second member 3, in this embodiment if the invention, further comprises a second member distal side edge 73 extending from the second member second distal termination point 65 to the second member second end 5. Preferably, the second member distal side edge 73 comprises a second member first distal edge section 74 adjacent to the second member second distal termination point 65 and extending to a point more proximate to the second member second end and may be slanted from a distal position at the second member second distal termination point 65 to a more forward position at a second member third distal termination point 75, i.e. slanted towards the centerline 24 of the second member. Adjacent to the second member first distal edge section 74 is a second member second distal edge section 76, which extends to a second member fourth distal termination point 77. Adjacent to the second member second distal edge section 76 is a second member third distal edge section 78 which extends to the second member second end 51 and is generally parallel to a centerline 24. In a preferred embodiment, because the second member first distal edge section 74 is slanted with respect to the centerline of the second member and the second member third distal edge section 78 is generally parallel to the centerline 24, the second member second distal edge section 76 may have curvature to provide a curved surface to join the second member first distal edge section 74 and second member third distal edge section 78 such that the second member distal side has a continuous curved surface without any sharp edges joining the sides.

Referring to the drawings, particularly FIGS. 2-4, each of the continuous sides of the second member forward circular element and second member distal circular element, as well as the second member center section side have upper longitudinally curved sections (79a, 79b and 79c) and lower longitudinally curved sections (80a, 80b, and 80c) which provide the sides with concave curvature. Also the edges of the second member forward side and second member distal side have upper longitudinally curved sections (81a and 81b) and lower longitudinally curved sections (82a and 82b). These longitudinally curved sections provide the sides and edges of the first member with concave curvature and an uninterrupted longitudinal curve which allow the bone plates to fit snugly against the curvature of the bone structure. The second end, however, may not have longitudinally curved sections.

Figure 5:
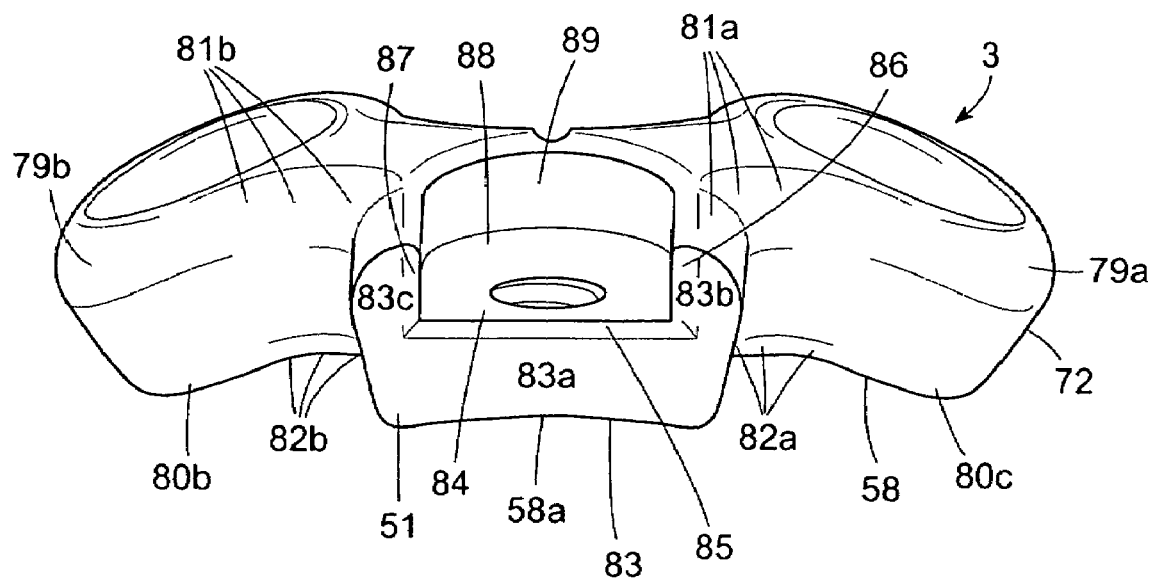
FIG. 5 is an end view of a second member of an adjustable bone plate in accordance with an embodiment of the invention.
Figure 6:
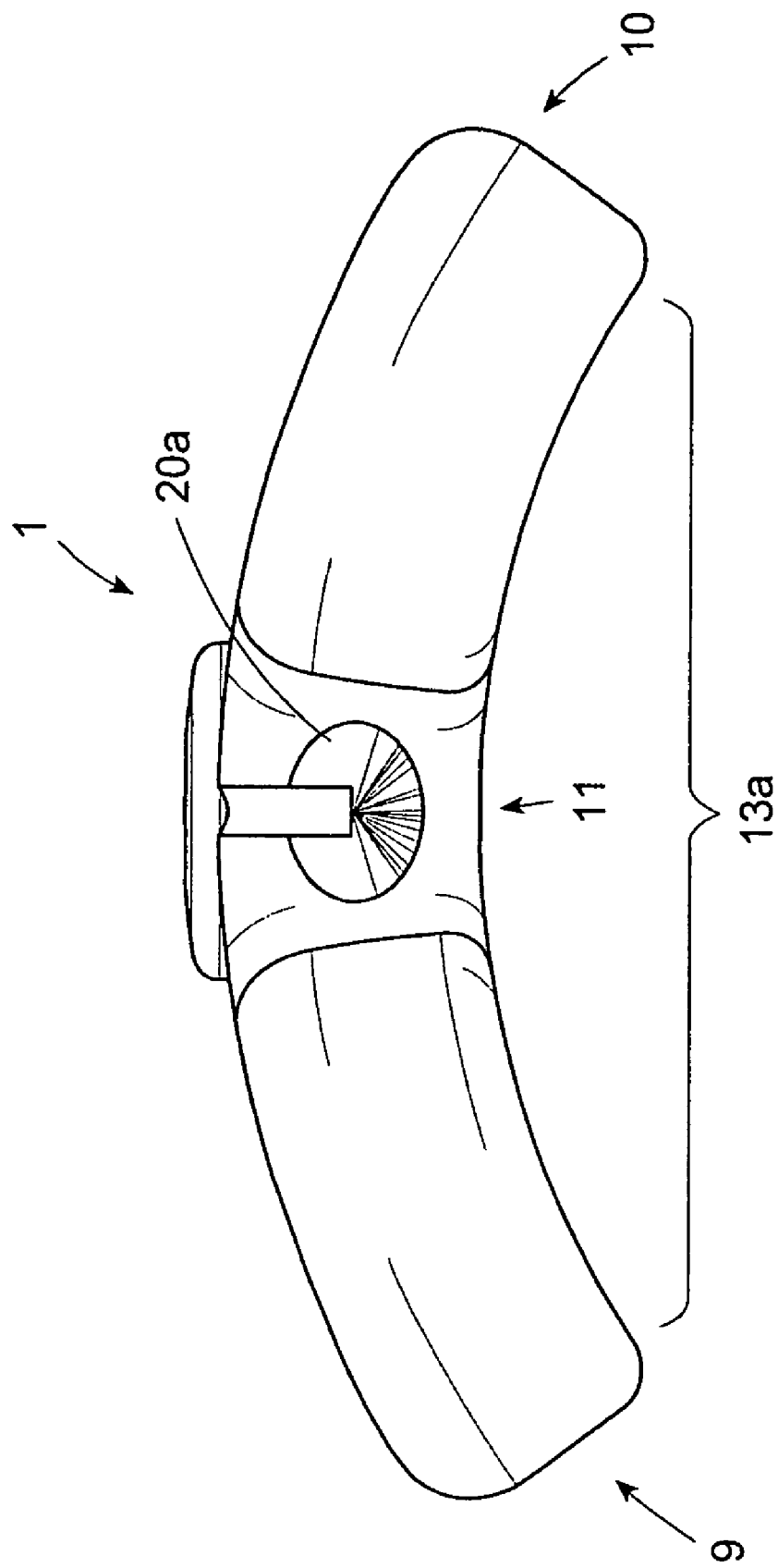
FIG. 6 is an end view of an adjustable bone plate in accordance with an embodiment of the invention.
Figure 7:
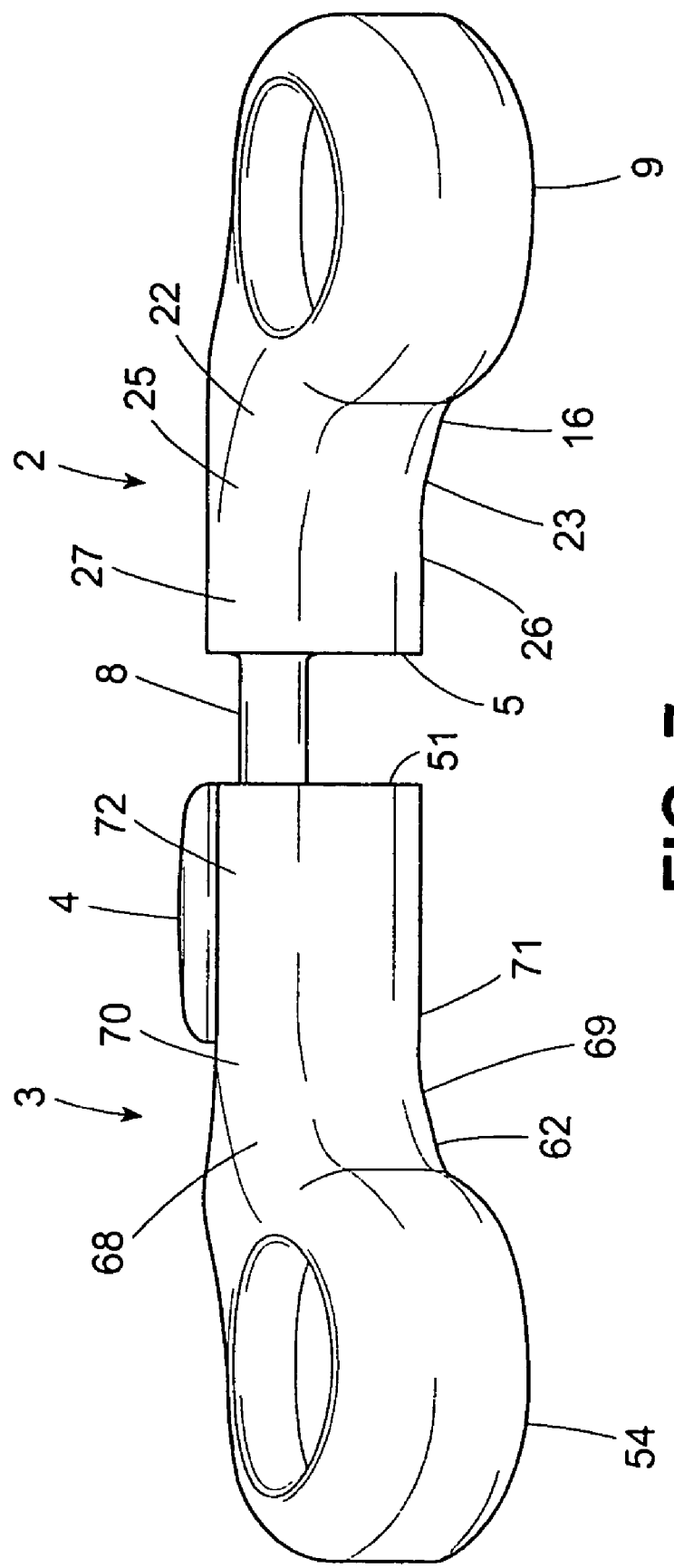
FIG. 7 is a side view of an adjustable bone plate in accordance with an embodiment of the invention.
Figure 17:
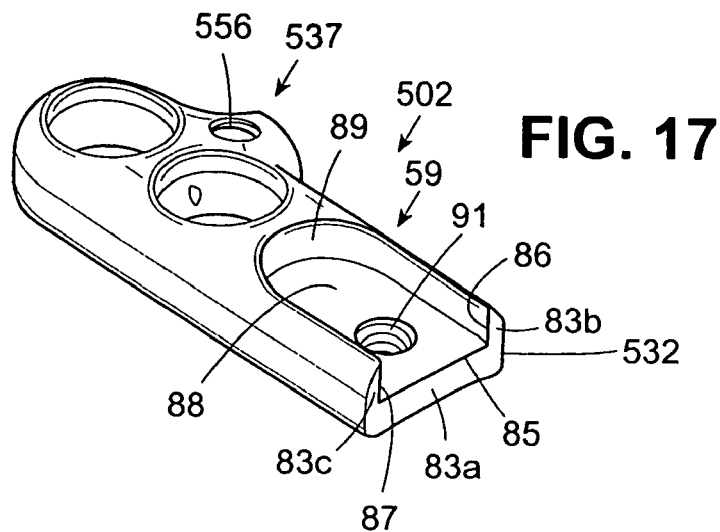
FIG. 17 is a perspective view of first member of an adjustable bone plate in accordance with an embodiment of the invention.
Figure 18:
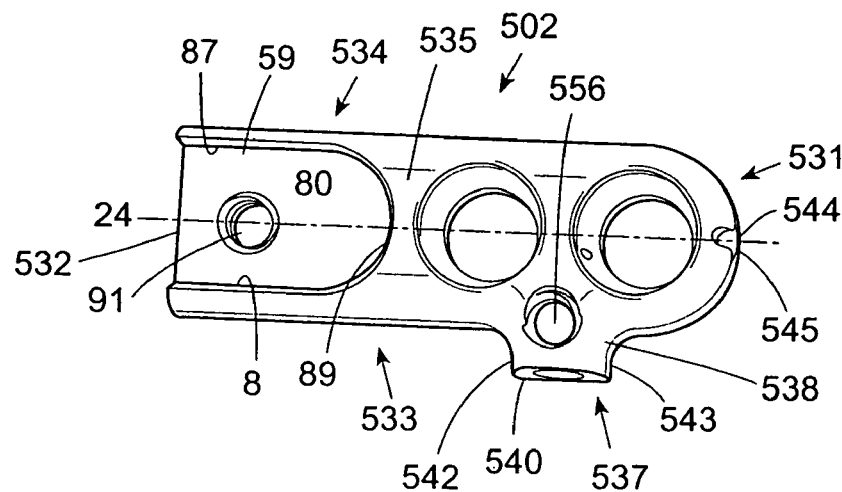
FIG. 18 is a top view of first member of an adjustable bone plate in accordance with an embodiment of the invention.

The second member second end (51 and 532), as shown, for example in FIG. 5, and in FIGS. 16-18, comprises a second end surface 83 which comprises a bottom section 83a which extends from the second end forward side to the second end distal side proximate to the second end bottom 83 to the recess 59, particularly recess opening 84 and opposing forward upright section 83b and distal upright section 83c so that the second end, when observed from the second end of the second member, has a "U-shaped" appearance framing the recess opening 84. The forward upright section 83b extends, on the forward side of the second member, from the bottom section 83a to the top surface of the second member, and the distal upright section 83c extends on the distal side of the second member from the bottom section 83a to the top surface of the second member. The edge 85 of the bottom section 83a opposite the bottom surface of the second member, the edge 86 of the forward section 83b opposite the second member third forward edge section 72 and the edge 87 of the distal section 83c opposite the second member third distal edge section 78 define the recess opening 84 at the second end (51 and 532) of the second member.

The recess 59 of the second member extends from the recess opening 84 at the second end (51 and 532) to a point between the second end (51 and 532) of the second member to the first end (50 and 531) of the second member. The recess which is shown in FIGS. 2 and 5 and also in FIGS. 16-18, for example, is defined by a recess bottom surface 88 and a recess wall 89. The recess wall 89 may be continuous and extending from the edge 86 of the forward section 83b and the edge 87 of the distal section 83c. The recess may have any geometric shape, however, as shown in the figures, the recess wall may have a forward recess wall 89a and an opposed distal recess wall 89b each extending from the second end (51 and 532) of the second member to a point between the second end (51 and 532) and first end (50 and 531) of the second member with a joining recess wall 89c there between. In an embodiment of the invention, the joining recess wall is arcuate having a convex curvature having a distant point 90, i.e. the point of the recess joining wall 89c most distant from the second end 51. In the embodiment of the invention shown in FIGS. 1-7, this is proximate to the second member curved end 66 of the first end, at about the centerline 24 of the second member. Preferably the forward recess wall and distal recess wall are about equidistant from the centerline 24 of the second member. The shape of the recess should complement the shape of the flange such as, as shown in the drawings, the flange having convex curvature which is accommodated by the convex curvature of the joining recess wall.

In the embodiment of the invention shown in the drawings, the second member further comprises a locking means bore 91 within the recess, which extends from the recess bottom surface 88 to a point between the recess bottom surface 88 to the bottom surface 58 of the second member, and may extend through the bottom surface 58. The locking means bore is defined by a locking means bore wall 91a. In an embodiment of the invention, the locking means bore is threaded. The locking means bore interacts with the locking means as shall be discussed below.

The second member comprises one or more bone screw bores. In the embodiment of the invention shown in FIGS. 1-7, the second member comprises a second member forward bone screw bore 92 proximate to the second member forward circular element 54, and a second member distal bone screw bore 93, proximate to the second member distal circular element 63. The second member forward bone screw bore 92 extends from the upper surface to the lower surface of the first member and is defined by second member forward bone screw bore inner wall 92*a* there between. The second member distal bone screw bore 93 extends from the upper surface to the lower surface of the first member and is defined by second member distal bone screw bore inner wall 93*a* there between. The bone screw bores are generally cylindrical and when a bone screw or other bone attachment means is inserted into the bone screw bore, the top surface of the bone screw or other bone attachment means is flush, or about flush, with the upper surface of the longitudinal plate such that they are recessed into the second member longitudinal plate. Also, the bone screws, or other bone attachment means will lock with the bone screw bores and also the bone of the patient.

As discussed above, the second member has curvature in that the second member bottom surface comprises the second member bottom surface curved section which is generally a concave arcuate section shown, for example, as 58 in FIG. 5. This means that the upper surface has a convex appearance and the second member when observed from the end has a curved appearance. Because the second member has curvature, in the embodiment of the invention shown in FIGS. 1-7, when bone screws or other bone attachment means are inserted into the second member forward bone screw bore 92 and the second member distal bone screw bore 93, the ends of the bone screws or other bone attachment means within the bone point towards each other, e.g., toe, which provides greater assurance that the bone screws or other bone attachment means will not pull out of the bone. This arrangement may also inhibit twisting of the bone plate.

Figure 8:
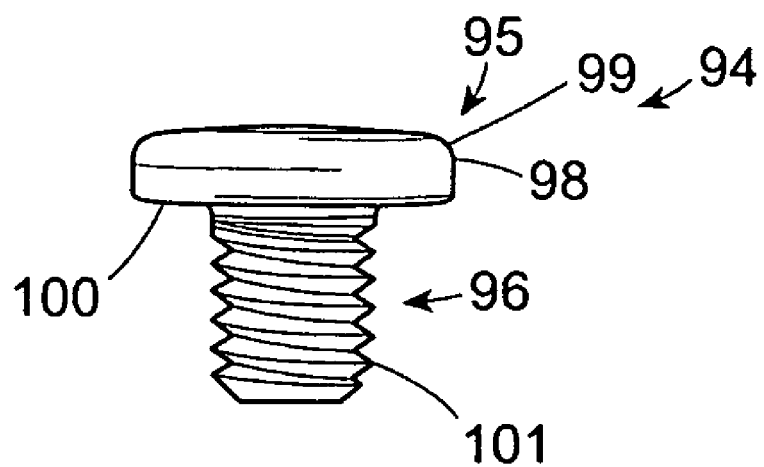
FIG. 8 is a front view of a locking means in accordance with an embodiment of the invention.
Figure 9:
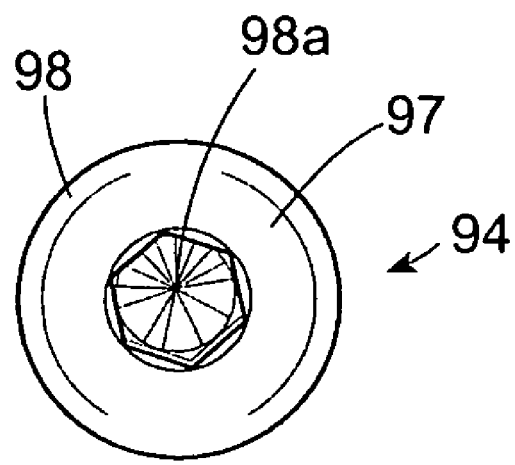
FIG. 9 is a top view of a locking means in accordance with an embodiment of the invention.

The locking means may be any device or apparatus capable of releaseably securing the first member and the second member such that the flange of the first member may translate within the recess of the second member, such as by having the flange slide within the recess, and be secured when the bone plate is at a therapeutically appropriate longitudinal length. Any of the locking means described above may be used in conjunction with the flange and recess in the embodiment of the bone plates shown in FIGS. 1-7, as well as in the other drawings. An example of a locking means useful in the invention is shown particularly in FIGS. 8-9. The locking means 94 comprises a top section 95 and a bottom section 96. The top section 95 comprises an upper surface 97, a top section body 98 which has an oversized element outer surface 99 and a bottom surface 100. The top section is generally cylindrical and has a dimension that is greater in a longitudinal direction than the bottom section 96, such that the locking means 94 has the appearance of a large top set screw. The bottom section 96 comprises a shaft 101, which is preferably, as shown in FIGS. 8-9, threaded to mate with the locking means bore 91 and releaseably secures the locking means to the second member when releaseably securing the first member and second member to each other to form the bone plate, as shall be discussed in more detail below. The shaft 101 has an end attached to or integral with the top section 95 and extends from the bottom surface 100 of the top section body 98, preferably at about the center, or at the center, of the bottom surface 100 to the lower end 102 of the shaft. The locking means may further have a recessed section 98*a* to accommodate a tool for tightening the locking means. For example, the recessed section 98 may be configured as a hex, as shown, or may be slotted or cruciform.

The first and second members are assembled into a bone plate, or a component of a bone plate wherein the bone plate comprises two or more sets of first member and second member, by arranging the first member and second member such that the flange is capable of sliding within the recess. The locking means is translated through the opening of the flange and through the locking means bore. Because the opening is generally oval or oblong, the flange is capable of sliding within recess in a longitudinal direction after the locking means is applied to the locking means bore of the second member provided the locking means is not tightened against the flange upper surface. Thus, the locking means may be translated through the opening and locking means bore and maintained at a position wherein the flange is capable of sliding within the recess thereby allowing the surgeon to select a longitudinal length by moving the first member and/or second member because the opening of the flange has a larger dimension than the bottom section of the locking means. The top section of the locking means has a larger dimension than the opening of the flange such that the bottom surface of the top section of the locking means is at least partially in contact with the flange upper surface. The locking means functions like a set screw in that once a longitudinal dimension of the bone plate is obtained, the locking means may be tightened by further translating the locking means within the locking means bore so that the flange applies pressure to the recess with the bottom surface of the locking means applying pressure to the top surface of the flange which inhibits or precludes the flange from further sliding within the recess thereby fixing the longitudinal length of the bone plate and setting the bone in place.

As shown in the drawings, the flange 8 is oriented on the second end of the first member so that it may interact with the recess 59 such that the upper surfaces of the first member and second member and bottom surfaces of the first member and second member are aligned to provide that the top and bottom of the bone plate are continuous or approximately continuous. That is that the top surface of the bone plate and bottom surface of the bone plate are approximately at the same longitudinal plane. Also, in a preferred embodiment of the invention, the recess, flange and locking means have dimensions such that the upper surface of the top section of the locking means does not extend above, or substantially above, the upper surfaces of the first member and second member of the assembled bone plate to provide the top surface of the assembled bone plate with a smooth surface.

A further embodiment of the invention is shown in FIGS. 10-19, in which the bone plate assembly 500 comprises two sets of a first member 501 and a second member 502 joined by first bridging means 503 and second bridging means 504. In this embodiment of the invention, the bone plate assembly 500 comprises an observation window 505 defined by the opposing sets of first member and second member and the first bridging means and second bridging means. The bone plate assembly in this embodiment of the invention may be adjusted in both the longitudinal dimension, i.e. longitudinal length, through the attaching means and/or locking means, and in the lateral dimension by the bridging means.

Referring particularly to FIG. 19, in this embodiment of the invention each first member 501 of the bone plate assembly 500 comprises a first member first end 506, a first member second end 507, a first member forward side 508 and a first member distal side 509. As shown in the drawings, for example FIGS. 11 and 12, each first member 501 also comprises a first member upper surface 510 and a first member lower surface 511. The first member lower surface 511 of each first member comprises a first member lower surface curved section 511*a* (shown for example in FIG. 14) which is generally a concave arcuate section which, as discussed above, facilitates the snug fit of the first member and adjustable bone plate against the curvature of the bone structure.

The first member 502 further comprises a first member protuberance 512 which extends from the first member forward side 508 at a point between the first member first end 506 and first member second end 507. As shown in FIGS. 16 and 19, for example, the first member protuberance 512 comprises a top surface 513 which is generally contiguous with, and an extension of, the first member upper surface 510 and a bottom surface 514 which is generally contiguous with, and an extension of, the first member lower surface 511. The first member protuberance 512 comprises a first member protuberance end wall 514. The first member protuberance 512 comprises a first member bridging rod bore 515 which has a first member bridging rod bore opening 515a at the first member protuberance end wall 514. The first member bridging rod bore 515 is defined by the first member bridging rod bore wall 515b which extends from the first member bridging rod bore opening 515a to a point between the first member forward side 508 and first member distal side 509 of the first member. The first member protuberance further comprises a first side wall 522 and second side wall 523 which extend from the first member forward wall to the first member protuberance end wall.

The first end of each first member comprises lateral curvature having an upper arc point 516 about equidistant from the first member forward side 508 and first member distal side 509 generally about the centerline 24 of each first member. The first member first end comprises a locking slot 517 at about the upper arc point 516. In addition, the first member first end comprises a first end upper longitudinally curved surface 518 and a first end lower longitudinally curved surface 519. The locking slot may be engaged by closure means provided with plate assembly, to assist in moving of the first member and second member together, i.e. to adjust the longitudinal dimension.

The first member forward side 508 of each first member comprises a forward side upper longitudinally curved surface 520 and a forward side lower longitudinally curved surface 521. Also, the first member distal side 509 of each first member comprises a distal side upper longitudinally curved surface 513 and a distal side lower longitudinally curved surface 514. Likewise the first side wall of the first member protuberance may, optionally, have an upper longitudinally curved surface 524 and a lower longitudinally curved surface 525, and the second side wall of the first member protuberance may, optionally, have an upper longitudinally curved surface 526 and a lower longitudinally curved surface 527. The forward side upper longitudinally curved surface, forward side lower longitudinally curved surface, the distal side upper longitudinally curved surface and distal side lower longitudinally curved surface, together with the first end upper longitudinally curved surface and a first end lower longitudinally curved surface provide each first member with an uninterrupted longitudinal curve, and with similar features on the second member provide the bone plate assembly with an uninterrupted longitudinal curve. The first side wall of the first member protuberance upper longitudinally curved surface 524 and a lower longitudinally curved surface 525, and the second side wall of the first member protuberance upper longitudinally curved surface 526 and a lower longitudinally curved surface 527 also add to this feature of the first member and the bone plate assembly in this embodiment of the invention.

The first member second end 507 in this embodiment of the invention has flange 8 protruding there from. The first member second end 507 and flange 8 in this embodiment of the invention have the same structure, elements and function as discussed above. In FIGS. 10-19, these elements of the first member 501 are provided the same element numbers as set forth in FIGS. 1-9, and reference is made to the description of these features above for these elements applicable to these features of the first member 501 in this embodiment of the invention.

The first member further comprises a retaining pin bore 528 which is proximate to the first member protuberance 512. The retaining pin bore 528 is defined by a retaining pin bore wall and has an upper opening at the first member top surface and/or first member protuberance and a lower opening at the first member bottom surface and/or first member protuberance. The retaining pin bore extends from the upper opening to the lower opening and preferably bisects the bridging means bore. The retaining pin bore may be threaded at one or both ends.

The first member also comprises one or more bone screw bores, which are defined by bone screw bore walls and extend from an opening at the upper surface of the first member to the lower surface of the first member. The bone screw bores of the first member in this embodiment of the invention have the same structure, elements and function as described above with respect to other embodiments of the invention. As shown in FIGS. 11-19, each first member 501 of the bone plate assembly 500 has a first bone screw bore 529 proximate to first end and a second bone screw bore 530 proximate to the second end.

As shown particularly in FIGS. 17 and 18, the second member 502 in this embodiment of the invention comprises a second member first end 531, a second member second end 532, a second member forward side 533 and a second member distal side 534. As shown in the drawings, for example FIGS. 11 and 12, each second member 502 also comprises a second member upper surface 535 and a second member lower surface 536. The second member lower surface 536 comprises a second member lower surface curved section 536a (shown, for example, in FIG. 14) which is generally a concave arcuate section which, as discussed above, facilitates the snug fit of the second member and adjustable bone plate against the curvature of the bone structure.

The second member 502 further comprises a second member protuberance 537 which extends from the second member forward side 533 at a point between the second member first end 531 and second member second end 532. As shown in FIGS. 16-18, for example, the second member protuberance 537 comprises a top surface 538 which is generally contiguous with, and an extension of, the second member upper surface 535 and a bottom surface 539 which is generally contiguous with, and an extension of, the second member lower surface 536. The second member protuberance 537 comprises a second member protuberance end wall 540. The second member protuberance 537 comprises a second member bridging rod bore 541 which has a second member bridging rod bore opening 541a at the second member protuberance end wall 540. The second member bridging rod bore 541 is defined by the second member bridging rod bore wall 541b which extends from the second member bridging rod bore opening 541a to a point between the second member forward side 533 and second member distal side 534. The second member protuberance further comprises a first side wall 542 and second side wall 543 which extend from the second member forward wall to the second member protuberance end wall.

The second member first end 531 has the same features and function as the first end of the first member as discussed above in this embodiment of the invention. Thus, the second member first end comprises lateral curvature having an upper arc point 544 about equidistant from the second member forward side 533 and second member distal side 534 generally about the centerline of each second member. The second member first end comprises a locking slot 545 at about the upper arc point 544. In addition, the second member first end comprises a first end upper longitudinally curved surface 546 and a first end lower longitudinally curved surface 547. As discussed above, the locking slot which may be engaged by closure means provided with plate assembly, to assist in moving of the first member and second member together, i.e. to adjust the longitudinal dimension.

The second member forward side 533 and second member distal side 534 have the same longitudinal curvature as the first member forward side 508 and first member distal side 509 of the bone plate assembly 500. Thus, the second member forward side comprises a forward side upper longitudinally curved surface 548 and a forward side lower longitudinally curved surface 549. Also, the second member distal side 509 comprises a distal side upper longitudinally curved surface 550 and a distal side lower longitudinally curved surface 551. Likewise, the first side wall of the second member protuberance may, optionally, have an upper longitudinally curved surface 552 and a lower longitudinally curved surface 553 (shown, for example, in FIG. 12), and the second side wall of the second member protuberance may, optionally, have an upper longitudinally curved surface 554 and a lower longitudinally curved surface 555. The forward side upper longitudinally curved surface, forward side lower longitudinally curved surface, the distal side upper longitudinally curved surface and distal side lower longitudinally curved surface, together with the first end upper longitudinally curved surface and a first end lower longitudinally curved surface provide each second member with an uninterrupted longitudinal curve, and with similar features on the first member provide the bone plate assembly with an uninterrupted longitudinal curve. The first side wall of the second member protuberance upper longitudinally curved surface and lower longitudinally curved surface, and the second side wall of the second member protuberance upper longitudinally curved surface and a lower longitudinally curved surface also add to this feature of the second member and the bone plate assembly in this embodiment of the invention.

The second member second end 532 in this embodiment has the same structure, elements and functions as the second end of the second member in the other embodiments of the invention discussed above. Also, the second member has a recess proximate to the second member second end 532. The recess in this embodiment of the invention has the same structure, elements and function as discussed above with respect to other embodiments of the invention. Also, the second member comprises the locking means bore 91 within the recess which has the same structure, elements and function as discussed above with respect to other embodiments of the invention. In FIGS. 10-19, these elements of the second member 502 are provided the same element numbers as set forth in FIGS. 1-9, and reference is made to the description of these features above for these element numbers which is applicable to these features of the second member 502 in this embodiment of the invention.

The second member further comprises a bridging means locking bore 556 which is proximate to the second member protuberance 537. The bridging means locking bore 556 is defined by a bridging means locking bore wall, which may be threaded, and has an upper opening at the second member upper surface and/or top surface of the second member protuberance and a lower opening into the top of the second member bridging rod bore 541. The bridging means locking bore 556 extends from the upper opening to the lower opening and preferably bisects the bridging means rod bore.

The second member also comprises one or more bone screw bores, which are defined by bone screw bore walls and extend from an opening at the second member upper surface to the second member lower surface. The bone screw bores of the second member in this embodiment of the invention have the same structure, elements and function as described above with respect to other embodiments of the invention. As shown in FIGS. 11-19, each second member 502 of the bone plate assembly 500 has a first bone screw bore 557 proximate to second member first end and a second bone screw bore 558 proximate to the recess 89.

Figure 20:
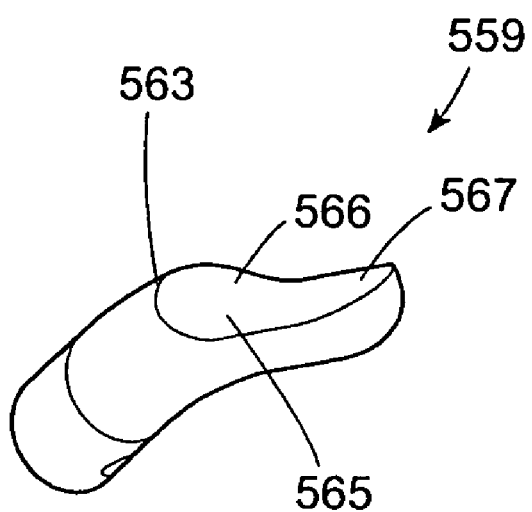
FIG. 20 is a perspective end view of a bridging means in accordance with an embodiment of the invention.
Figure 21:
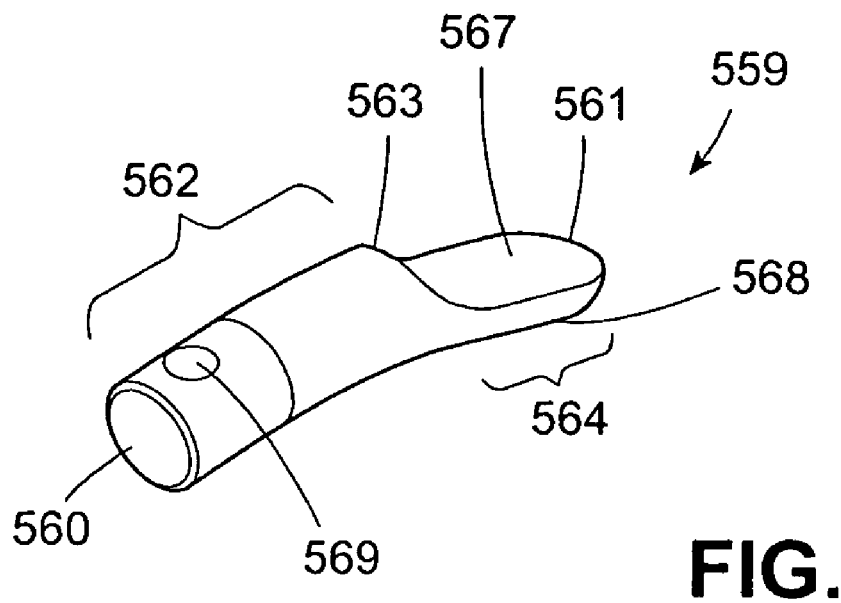
FIG. 21 is a perspective side view of a bridging means in accordance with an embodiment of the invention.

In the embodiment of the invention shown in FIGS. 10-19, the bone plate assembly 500 is assembled by connecting one set of attached first member and second member with another set of attached first member and second member by use of the bridging means. In this embodiment of the invention, the bridging means comprises a bridging rod 559. The bridging rod 559 is particularly shown in FIGS. 20 and 21. The bridging rod 559 has a generally cylindrically shape with a tapered section at one end. As shown the drawings the bridging rod 559 comprises a circular end 560 and a tapered end 561. The bridging rod comprises a cylindrical section 562 which has a continuous curved outer section providing the cylindrical section 562 with a cylindrical shape and extends from the cylindrical end 560 to the cylindrical section termination point 563, which is between the cylindrical end 560 and the tapered end 561. A tapered section 564 of the bridging rod 559 extends from the cylindrical section termination point 563 to the tapered end 559. The tapered section 564 comprises a top side 565 which has a slanted piece 566 and a level piece 567 with the slanted piece 566 extending from the cylindrical section termination point 563 to a first end of the level piece 567 and the level piece extends from its first end where it joins the slanted piece 566 to the tapered end 561 of the bridging rod 559. The tapered section further comprises a bottom side 568 which may, as shown in the drawings, be a continuation of the cylindrical curvature of the cylindrical section 562. The bridging rod may further comprise a retaining pin hole 569 proximate to the cylindrical end 560. The retaining pin hole is defined by a retaining pin hole wall and in embodiments of the invention wherein the bridging rod is solid, it extends from one point on the outer wall of the bridging rod to another point and in embodiments wherein the bridging rod is hollow, the retaining pin hole may be two holes which correspond to allow a retaining pin to extend from both holes in the bridging rod. The retaining pin and the retaining pin hole may be threaded such that the outer surface of the retaining pin has one or more threaded sections, or is continuously threaded from the top to the bottom, and the retaining pin hole wall is continuously threaded or comprises threaded sections.

A retaining pin 577 may be used in conjunction with the bone plate assembly 500. As shown in FIG. 16, for example, the retaining pin 577 generally comprises a first end 578, a second end 579 and an outer surface 580 which is a continuous curved surface between the first end 578 and second end 579 such that the retaining pin 577 is cylindrical in shape. The retaining pin 577 may be threaded or comprise threaded sections such that the outer surface comprises one or more threaded sections.

Figure 10:
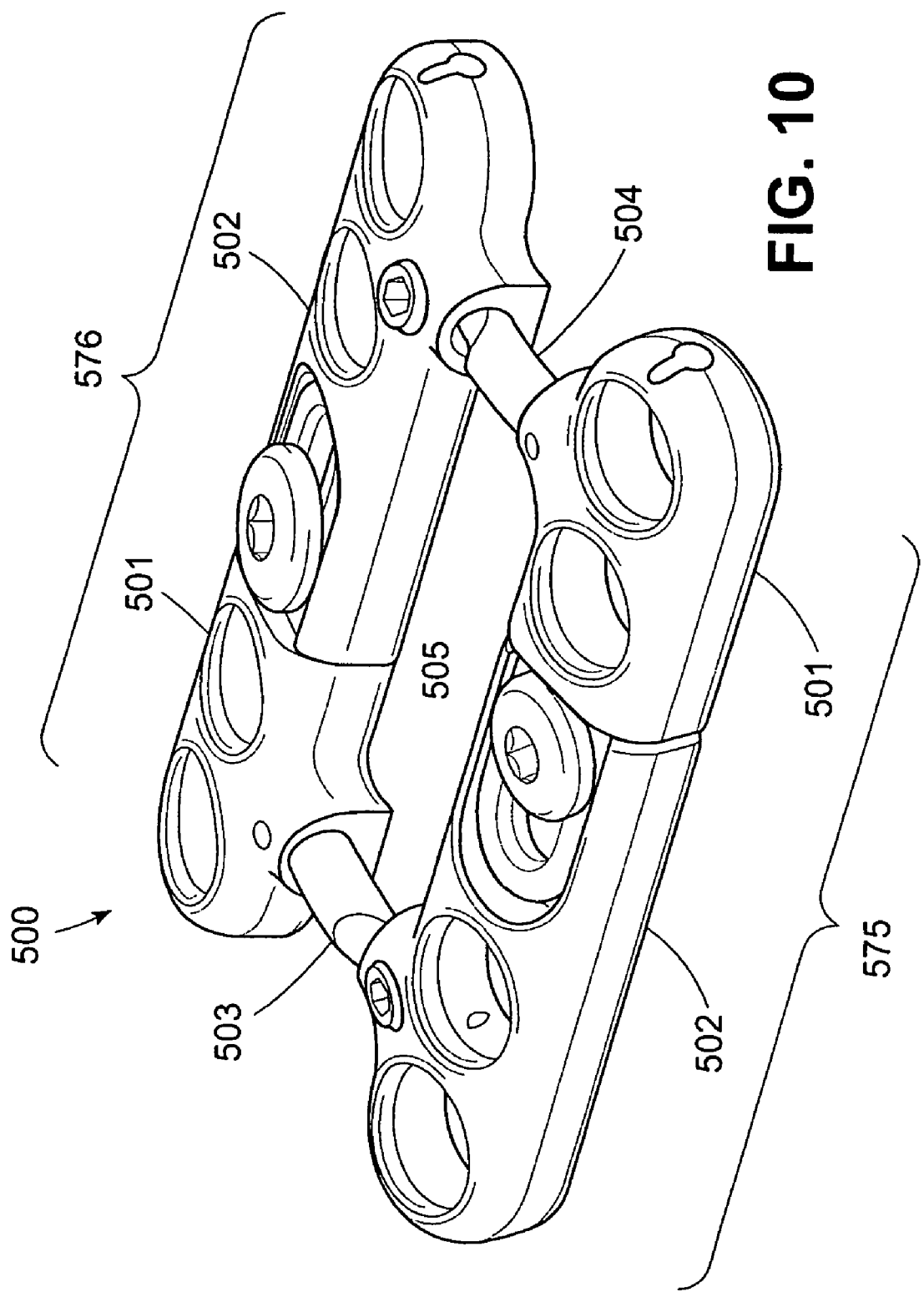
FIG. 10 is a perspective view of an adjustable bone plate in accordance with an embodiment of the invention.
Figure 11:
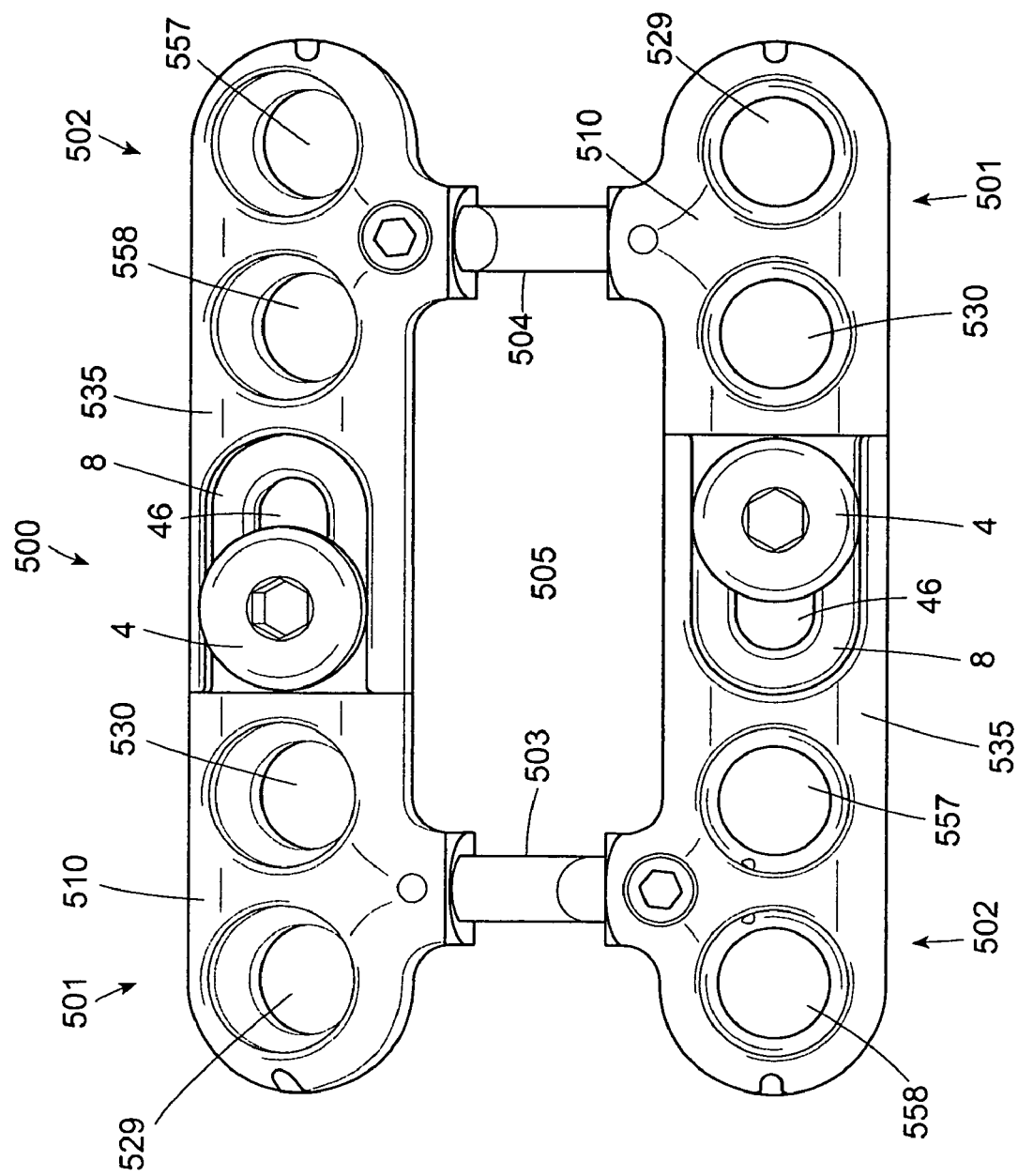
FIG. 11 is a top view of an adjustable bone plate in accordance with an embodiment of the invention.
Figure 12:
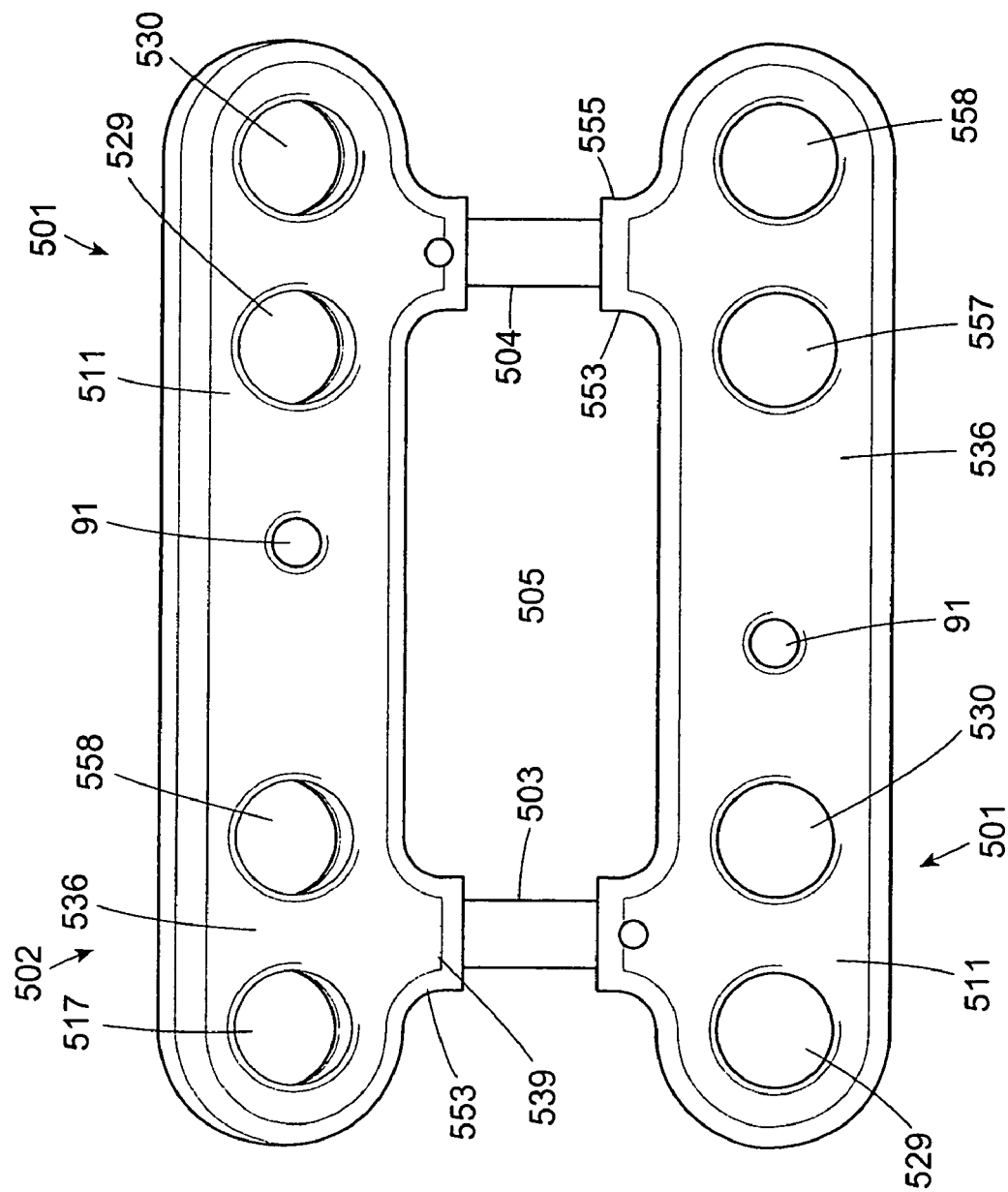
FIG. 12 is a bottom view of an adjustable bone plate in accordance with an embodiment of the invention.
Figure 15:
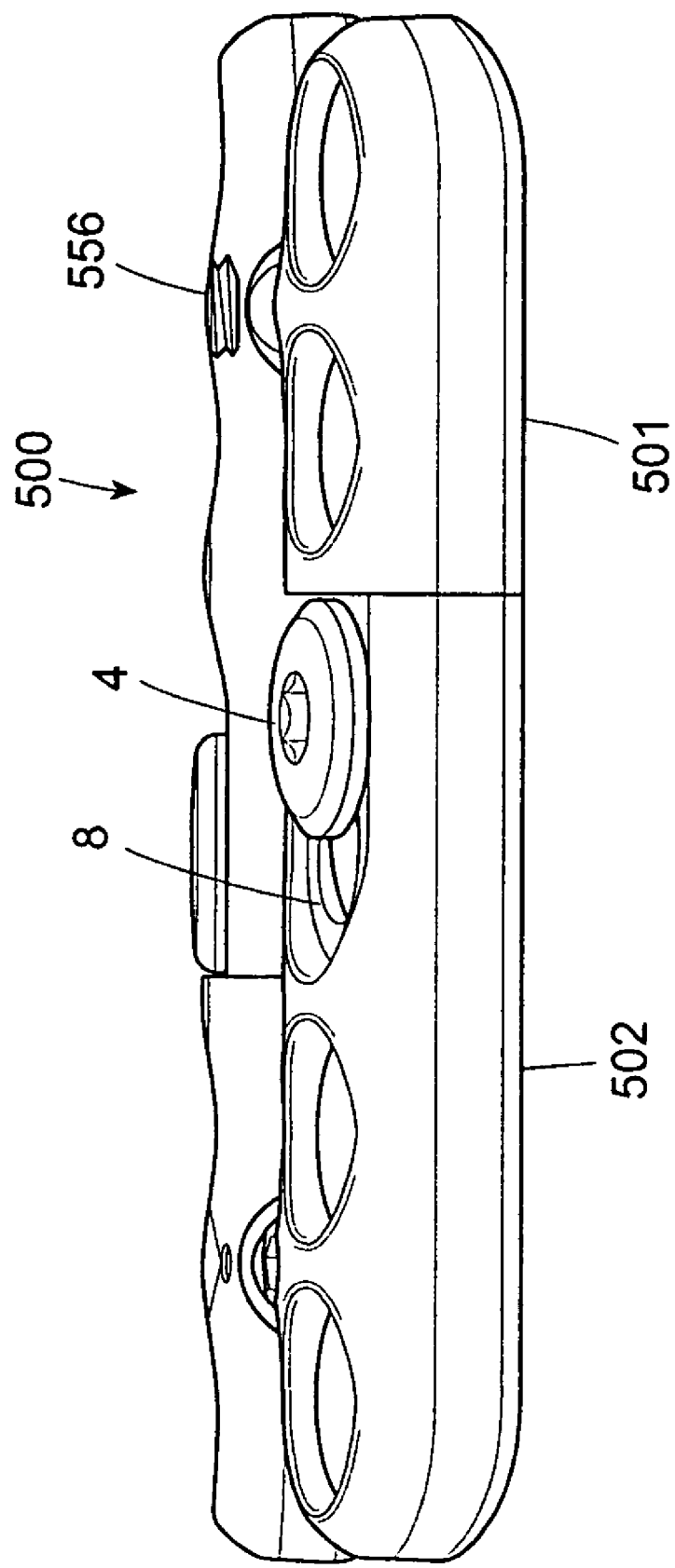
FIG. 15 is a side view of an adjustable bone plate in accordance with an embodiment of the invention.

The bridging means is generally used to join sets of first members and second members as shown in FIG. 10 for example. As shown in FIGS. 10 and 16, for example, the bridging means may comprise a bridging rod 559 used in conjunction with a bridge locking means which as shown in the drawings may be a set screw 570 having an upper end 571 and a lower end 572 and a continuous outer wall 573 there between. The continuous outer wall 573 is, preferably, threaded, although it may not be threaded. The upper end 571 may comprise a set screw recessed section 574 to accommodate a tool for tightening the bridge locking means. The bridging means is also used in conjunction with the retaining pin 577, the retaining pin bore 528 of the first member 501 and the retaining pinhole 569 of the bridging rod 559 to affix the bridging rod 559, proximate to the cylindrical end 560 to the first member 501.

The bone plate assembly, such as that shown in FIGS. 10-19, is generally assembled by first adjoining two sets of first members and second members by aligning the flange of the first member with the recess of the second member and then applying the locking means such that the locking means is translated through the opening of the flange and through the locking means bore of each set of first member and second member, in a similar fashion as discussed above with respect to the other embodiments of the invention. The same locking means as described above may be used. Once the sets of first members and second members are formed, the bridging means is applied by translating the bridging rod through the bridging means bores in the first member and second member. The bridging rod may be attached or releaseably secured to the first members and second members in adjoining first member and second member set through the use of retaining pins and bridge locking means, such as by translating the retaining pin through the retaining pin bore of the first member and retaining pinhole of bridging rod and translating the set screw through the bridge locking means bore such that it interacts with the bridging rod, particularly the level piece of the bridging rod.

Because the bridging rods are capable of sliding within the bridging rod bores in the first member and second member and the flanges are capable of sliding within the recesses of the second member, the assembled bone plate in the embodiment of the invention comprising bridging means has both longitudinal and lateral adjustability. The longitudinal dimension can be adjusted by sliding the flanges within the recess and when the desired longitudinal dimension is obtained, the locking means may be tightened to prevent further movement. Also, when the appropriate lateral dimension is obtained then the bridge locking means, such as set screw, can be applied and/or tightened to prevent further movement of the bridging rod within the bridging means bores. In a preferred embodiment of the invention, one end of the bridging rod is held into the first member by translating a retaining pin into the retaining pin bore of the first member and bridging rod, and the tapered end 561 of the bridging rod is free to move within the bridging means bore of the opposite second member. The lower surface 572 of the set screw applies pressure to the top surface of the level piece 567 to secure the bridging rod and prevent further movement thereby setting the lateral dimension of the bone plate assembly. When assembled, as shown in FIG. 10, for example, the second member of the first set of first member/second member is connected by the bridging means opposite to the first member of the second set of first member/second member, and the first member of the first set of first member/second member is connected by the bridging means opposite to the second member of the second set of first member/second member. It should be understood that more than two sets of first member/second member may be laterally secured to each other using bridging means.

The bone plate assembly shown in FIGS. 11-19 comprises a first set of first member/second member 575 and a second set of first member/second member 576. The first set 575 and second set 576 of first member/second member are connected by first bridging means 503 which connect the second member 502 of the first set 575 to the first member 501 of the second set 576 and by second bridging means 504 which connect the first member 501 of the first set 575 to the second member 502 of the second set 576. The various members and sets are connected and both longitudinally and laterally adjustable as discussed above.

The bridging rods may have curvature such that when connecting one or more sets of first members and second members, the assembled bone plate has curvature in that the bottom has a concave appearance and the top has a convex appearance. This can generally be seen with respect to the end view of the embodiment of the invention shown in FIG. 14. As shown in FIG. 14, the first set of the first member and second member and second set of the first member and second member each have a concave appearance on the bottom as shown with respect to the curvature of the first member lower surface curved section 511a and second member lower surface curved section 536a. As such, the entire bone plate has a bottom which has global bottom curvature 599 across the bottom of the assembled bone plate in this embodiment of the invention. Thus, when the bone plate is applied to the patient by translating bone screws or other bone attachment means through the bone screw bores of the first set of first member and second member and second set of first member and second member and securing the bone screws or other bone attachment means to the bone, the bone screws or other bone attachment means applied to the first set and bone screws or other bone attachment means applied to the second set will point towards each other, e.g. toe, which provides greater assurance that the bone screws or other bone attachment means will not pull out of the bone, and may inhibit twisting of the bone plate. Also, the global bottom curvature 599 facilitates the fit of the bone plate on the bone of a patient.

The invention comprises a method for setting the broken bone of a patient. The method comprises the steps of providing the first member, second member and locking means as described herein. In an embodiment of the invention, the second member is secured to the bone of the patient, on one side of the break, by translating bone screws or other bone attachment means through the second member forward bone screw bore 92 and a second member distal bone screw bore 93. The first member is secured to the bone of the patient, on the side of the break opposite to the side of the break where the second member is attached, by translating bone screws or other bone attachment means through the first member forward bone screw bore 48 and first member distal bone screw bore 49 with the flange 8 within the recess 59 such that the opening of the flange 8 is at least aligned with the locking means bore such that the locking means can be translated within both the opening 46 of the flange 8 and locking means bore 59. In the method, the locking means is translated through the opening 46 of the flange 8 and locking means bore 59 and the pieces of broken bone are moved proximate to each other for healing by adjusting the position of the first member and/or second member to set a longitudinal length or dimension of the bone plate. The first member and second member may be applied to the broken bone and the pieces of broken bone may be moved together, with the locking means then translated through the opening 46 of the flange 8 and the locking means bore 59 and tightened to prevent the flange from sliding within the recess and fix the longitudinal length or dimension of the bone plate to set the bone in place. Alternatively, however, the surgeon may translate the locking means through the opening 46 of the flange and locking means bore 91 without tightening the locking means so that the flange 8 may slide within the recess 59, then move the first and/or second member with the flange sliding within the recess to bring pieces of broken bone together and then tighten the locking means to inhibit or prevent further sliding of the flange within the recess thereby fixing the longitudinal length or dimension of the bone plate to set the bone in place.

In a further embodiment, the first member and second member may be assembled into the bone plate prior to applying the bone plate to the broken bone of a patient. In this embodiment, the method involves translating the locking means through the opening 46 and locking means bore 91 without tightening the locking means to preclude the flange 8 from sliding within the recess 59 prior to applying the bone plate or either the first member or second member to a patient. Next, the assembled bone plate is applied to the broken bone of a patient by placing the first member over the one side of the break and placing the second member over the bone on the opposite side of the break and securing the bone plate to the patient by translating bone screws or other bone attachment means through the first member forward bone screw bore 48 and first member distal bone screw bore 49 and translating bone screws or other bone attachment means through the second member forward bone screw bore 92 and a second member distal bone screw bore 93, with the bone screws applied through the various bone screw bores in any order. The pieces of broken bone may be moved together and then the surgeon then tightens the locking means to prevent further sliding of the flange within the recess thereby fixing the longitudinal length of the bone plate and setting the bone in place. In yet another embodiment of the invention, the surgeon may releasably secure the first member and second member and apply the locking means to fix the longitudinal length of the bone plate prior to applying the bone plate to the broken bone of a patient.

An implant procedure with two ends of bone properly aligned may be described as follows:
1. Loosely assembly the first member and second member with the locking means loosely tightened to allow the flange to move within the recess.
2. Translate one bone screw through a bone screw bore in either the first member or second member and into the bone.
3. With assembly fully extended, translate a second bone screw into a bone screw bore of either the first member or second member (opposite of the one to which the bone screw is applied in step 2) and into the bone.
4. Implant bone screws into any remaining bone screw bores of the first member and/or second member.
5. Compress the first member and second member (i.e., move the members toward each other) to set the bone in place and tighten the locking means to prevent further movement of the first member and second member.

The method may further comprise providing one or more bridging means to apply one or more first member and second member sets to a broken bone of a patient such that the bone plate assembly has both longitudinal and lateral adjustability. In this embodiment, which may generally concern applying the bone plate shown in FIGS. 10-19, a first member 501 is applied to a broken bone and a second member 502 is applied to the broken bone using bone screws or other bone attachment means translated through one or more bone screw bores on the first member and second member with the flange 8 of the first member 501 within the recess 59 of the second member 502, optionally with the locking means applied and loosely tightened to allow movement of the first member and/or second member, thus forming a first first member and second member applied to the bone, such as that discussed above with respect to the embodiment shown in FIGS. 1-8. Next, a first bridging means is translated into a bridging means bore, such as the second member bridging rod bore 541, and a second bridging means is translated into a bridging means bore, such as a first member bridging rod bore 515, which may be held by a retaining pin. A second first member and second member set may then be applied over a side of the break opposite the break or breaks on the bone. This is accomplished by translating the first bridging means within a bridging means bore, such as a first bridging rod bore 518 of the first member of the second first member and second member set, which may be held by a retaining pin, and translating the second bridging means in bridging means bore, such as a second bridging rod bore 541, of the second member of the second first member and second member set in a manner in which the flange of the first member is within the recess of the second member of the second first member and second member set, as discussed above with respect to the first first member and second member set. The first member and second member of the second first member and second member set may be secured to the bone by translating bone screws or other bone attachment means through some or all of the first member and second member bone screw bores of the second first member and second member set. The surgeon may then move the first member and second member of the first first member and second member set longitudinally with respect to each other, the first member and second member of the second first member and second member set longitudinally with respect to each other and the first first member and second member set and the second first member and second member set laterally with respect to each other in order to move the broken pieces of bone together. The bone may then set the bone in place for healing by applying the locking means to fix the longitudinal dimension of both the first first member and second member set and second first member and second member set as discussed above by use, for example, of a large top screw, and apply the bridge locking means to set the lateral dimension of the adjustable bone plate such as by translating a set screw within the bridging means locking bore 556 in each second member of each first member and second member set. The surgeon may observe the pieces of bone in the observation window. In a preferred embodiment of this method, the bridging means comprises the bridging rod and set screw. The surgeon may also fix the longitudinal and/or lateral dimensions of the bone plate prior to applying the bone plate to a broken bone of a patient.

The bone plate and its components may be constructed of any suitable biocompatible material known to have sufficient structural strength and durability, such as stainless-steel, alloys, cobalt alloys or titanium alloys, including any suitable ASTM or ISO standard materials as set forth on the United States Food and Drug Administration website. Some examples include unalloy titanium, titanium alloyed with aluminum, niobium and/or vanadium, stainless steels and other irons alloyed with molybdenum, chromium, cobalt, tungsten, nickel, manganese in various combinations, various other stainless steels or other iron alloys, such as, with aluminum oxides, zirconium oxides, tantalom and calcium phosphates. Any acceptable polymeric material may be used, such as PEEK (poly ethyl ethylketone), with sufficient flex to mimic the micromotion of normal bone, to stimulate bone growth. The PEEK may be combined with other materials or polymers. Also, ceramic filled biocompatible polymers, or other biocompatible materials of sufficient strength to stabilize the bone during healing, or correct a fracture of the bone may be used to make the bone plate, or any component or member of the bone plate. Other materials which may be used include bioabsorbable materials and collagen. One or more materials may be used in building, manufacturing and assembling the bone plates or any component of the bone plates. For example, combinations of the materials discussed herein may be used.

The bone plate or any component or member of the bone plate, may further comprise bioabsorbable drug delivery devices, such as implantable modular drug delivery devices. Examples of bioabsorbable drug delivery devices are described in the co-pending application, U.S. Ser. No. 11/135,256 filed May 23, 2005, IMPLANTABLE PROSTHETIC DEVICES CONTAINING TIMED RELEASE THERAPEUTIC AGENTS, which is incorporated herein in its entirety by reference. Such devices, for example, may be placed within a dedicated bore, such as a drug delivery bore, or within a bone screw bore or locking means bore. Accordingly, the bone plate can be used to deliver drugs, if needed.

Bioabsorbable surgical fasteners or bone screws made from bioabsorbable materials may be used to apply the bone plate, i.e. to apply the first member and/or second member, to the bone of a patient. For example, the materials described in the co-pending patent application, U.S. Ser. No. 11/025,231, filed Dec. 29, 2004, SURGICAL FASTENERS AND RELATED IMPLANT DEVICES HAVING BIOABSORBABLE COMPONENTS, which is incorporated herein in its entirety by reference, may be used for the bone screws and the bone screws may be the surgical fasteners described in this co-pending patent application.

What is claimed is:

1. A bone plate comprising one or more sets of first members and second members wherein in each set the first member is releaseably secured to the second member by attachment means which allows longitudinal adjustment of the first member and second member in relation to each other and locking means which restricts or inhibits movement of the first member and second member, wherein the attachment means comprises a flange in the first member or second member and a complimentary shaped recess defined by a recess wall in the first member or second member that does not comprise the flange, wherein the flange slides within the recess, and wherein the recess is open in the direction of the top of the plate, wherein the flange comprises an opening and the first member or second member which does not comprise the flange has a locking means bore proximate to the recess and the locking means is translated through the opening and the locking means bore, wherein the first member comprises a first member first end, a first member second end, a first member forward side and a first member distal side and the second member comprises a second member first end, a second member second end, a second member forward side and a second member distal side and wherein i) the first member has a second end surface at the first member second end with the a flange protruding from the second end surface the flange having a flange forward side, a flange distal side, a flange end, a flange upper surface and flange lower surface wherein the flange forward side is opposed and parallel to the flange distal side with the flange end there between perpendicular to the flange forward side and flange distal side and opposite to the second end surface and ii) the second member comprises a recess opening at the second member second end with the recess defined by a recess bottom surface and the recess wall, wherein a) the first member first end comprises
  i) a first member forward circular element, a first member first forward termination point and a first member second forward termination point with the first member forward circular element having a continuous side from the first member first forward termination point to the first member second forward termination point;
  ii) a first member distal circular element, a first member first distal termination point and a first member second distal termination point with the first member distal circular element having a continuous side from the first member first distal termination point to the first member second distal termination point; and
  iii) a first member center section adjacent to the first member first forward termination point and the first member first distal termination point which extends from the first member first forward termination point to the first member first distal termination point; and
b) the second member first end comprises
  i) a second member forward circular element, a second member first forward termination point and a second member second forward termination point with the second member forward circular element having a continuous side from the second member first forward termination point to the second member second forward termination point;
  ii) a second member distal circular element, a second member first distal termination point and a second member second distal termination point with the second member distal circular element having a continuous side from the second member first distal termination point to the second member second distal termination point; and
  iii) a second member center section adjacent to the second member first forward termination point and the second member first distal termination point which extends from the second member first forward termination point to the second member first distal termination point, and wherein a) the first member further comprises a first member third forward termination point, a first member fourth forward termination point, a first member third distal termination point and a first member fourth distal termination point and a centerline about equidistant from the first member forward side and the first member distal side wherein i) the first member forward side is comprised of a first member forward side edge having a first member first forward edge section adjacent to the first member second forward termination point extending to the first member third forward termination point slanted towards the centerline of the first member, a first member second forward edge section adjacent to the first member first forward edge section which extends from the first member third forward termination point to the first member fourth forward termination point and adjacent thereto a first member third forward edge section which extends from the first member fourth forward termination point to the first member second end and is generally parallel to the centerline of the first member and ii) the first member distal side is comprised of a first member distal side edge having a first member first distal edge section adjacent to the first member second distal termination point extending to the first member third distal termination point slanted towards the centerline of the first member, a first member second distal edge section adjacent to the first member first distal edge section which extends from the first member third distal termination point to the first member fourth distal termination point and adjacent thereto a first member third distal edge section which extends from the first member fourth distal termination point to the first member second end and is generally parallel to the centerline of the first member, and b) the second member further comprises a second member third forward termination point, a second member fourth forward termination point, a second member third distal termination point and a second member fourth distal termination point and a centerline about equidistant from the second member forward side and the second member distal side wherein i) the second member forward side is comprised of a second member forward side edge having a second member first forward edge section adjacent to the second member second forward termination point extending to the second member third forward termination point slanted towards the centerline of the second member, a second member second forward edge section adjacent to the second member first forward edge section which extends from the second member third forward termination point to the second member fourth forward termination point and adjacent thereto a second member third forward edge section which extends from the second member fourth forward termination point to the second member second end and is generally parallel to the centerline of the second member and ii) the second member distal side is comprised of a second member distal side edge having a second member first distal edge section adjacent to the second member second distal termination point extending to the second member third distal termination point slanted towards the centerline of the second member, a second member second distal edge section adjacent to the second member first distal edge section which extends from the second member third distal termination point to the second member fourth distal termination point and adjacent thereto a second member third distal edge section which extends from the second member fourth distal termination point to the second member second end and is generally parallel to the centerline of the second member.

* * * * *